United States Patent
Matsumoto

(10) Patent No.: US 7,153,664 B2
(45) Date of Patent: Dec. 26, 2006

(54) SIGNAL TRANSDUCTION PROTEIN TAB2

(76) Inventor: Kunihiro Matsumoto, Rorerukoto Showataomocho 201, 2-44, Taomo-cho, Showa-ku, Nagoya-shi, Aichi 466-0801 (JP)

(*) Notice: Subject to any disclaimer, the term of this patent is extended or adjusted under 35 U.S.C. 154(b) by 34 days.

(21) Appl. No.: 10/151,569

(22) Filed: May 20, 2002

(65) Prior Publication Data

US 2003/0040050 A1 Feb. 27, 2003

(51) Int. Cl.
  *G01N 33/53* (2006.01)
  *C12P 21/06* (2006.01)
  *C12N 15/74* (2006.01)
  *C12N 5/02* (2006.01)
  *C07H 21/04* (2006.01)

(52) U.S. Cl. ............... 435/7.21; 435/69.1; 435/320.1; 435/325; 536/23.5; 536/24.3; 530/350

(58) Field of Classification Search ............. 435/69.1, 435/320.1, 325, 7.21; 536/23.5, 24.3; 530/350
See application file for complete search history.

(56) References Cited

U.S. PATENT DOCUMENTS

| | | |
|---|---|---|
| 5,837,819 A | 11/1998 | Matsuomoto et al. |
| 5,989,862 A | 11/1999 | Matsuomoto et al. |
| 6,140,042 A | 10/2000 | Matsuomoto et al. |
| 2002/0119525 A1 | 8/2002 | Matsuomoto et al. |

FOREIGN PATENT DOCUMENTS

| | | |
|---|---|---|
| EP | 0 803 571 A2 | 10/1997 |
| JP | 10-4976 | 1/1998 |

OTHER PUBLICATIONS

Sambrook, J., et al. Molecular Cloning. 1989.*
Tan et al. Journal of Drug Targeting, 2003, vol. 10(2), pp. 153-160.*
Cao et al., "TRAF6 is a signal transducer for interleukin-1", *Nature* 383:443-446 (1996).
Hillier et al., "Generation and Analysis of 280,000 Human Expressed Sequence Tags", *Genome Research* 6:807-828 (1996).
Nagase et al., "Prediction of the Coding Sequences of Unidentified Human Genes. XI. The Complete Sequences of 100 new cDNA Clones from Brain Which Code for Large Proteins *in vitro*", *DNA Research* 5:277-286 (1998).
Ninomiya-Tsuji et al., "The kinase TAK1 can activate the NIK-IkB as well as the MAP kinase cascade in the IL-1 signalling pathway", *Nature* 398:252-256 (1999).
Takaesu et al., "TAB2, a Novel Adaptor Protein, Mediates Activation of TAK1 MAPKKK by Linking TAK1 to TRAF6 in the IL-1 Signal Transduction Pathway", *Molecular Cell* 5:649-658 (2000).
Takaesu et al., "Interleukin-1 (IL-1) Receptor-Associated Kinase Leads to Activation of TAK1 by Inducing TAB2 Translocation in the IL-1 Signaling Pathway", *Molecular and Cellular Biology* 21:2475-2484 (2001).
European Search Report dated Feb. 13, 2004.
Ohara et al. EMBL Accession No. AB018276 (1998).
Poustka et al. EMBL Accession No. AL117407 (1999).
Shibuya et al. "TAB1" An Activator of the TAK1 MAPKKK in TGF-β Signal Transduction *Science* 272(5265):1179-1182 (1996).
Takaesu et al. "TAB2, a novel adaptor protein, mediates activation of TAK1 MAPKKK by linking TAK1 to TRAF6 in the IL-1 signal transduction pathway" *Molecular Cell* 5(4):649-658 (2000).
Shibuya, Functional role for TAB1-TAK1 in TGF-β signaling, *Seikagaku* 71:1205-1212 (1999) (with English translation).

* cited by examiner

*Primary Examiner*—Janet L. Andres
*Assistant Examiner*—Gregory S. Emch
(74) *Attorney, Agent, or Firm*—Fish & Richardson P.C.

(57) ABSTRACT

A novel signal transducer TAB2 which acts as an adapter molecule of TRAF6 and TAK1 and mediates the activation of TAK1 in the signal transduction of IL-1 was isolated. TAB2 induced the activation of NF-κB and JNK by IL-1. The signal transduction by IL-1 was inhibited by inhibiting the signal transduction of TAB2 with the use of a dominant negative mutant of TAB2. A compound inhibiting the signal transduction in TAB2 is useful as an anti-inflammatory drug.

69 Claims, 10 Drawing Sheets

```
MAQGSHQIDF QVLHDLRQKF PEVPEVVVSR CMLQNNNNLD ACCAVLSQES TRYLYGEGDL    60
NFSDDSGISG LRNHMTSLNL DLQSQNIYHH GREGSRMNGS RTLTHSISDG QLQGGQSNSE   120
LFQQEPQTAP AQVPQGFNVF GMSSSSGASN SAPHLGFHLG SKGTSSLSQQ TPRFNPIMVT   180
LAPNIQTGRN TPTSLHHGV PPPVLNSPQG NSIYIRPYIT TPGGTTRQTQ QHSGWVSQFN   240
PMNPQQVYQP SQPGPWTTCP ASNPLSHTSS QQPNQQGHQT SHVYMPISSP TTSQPPTIHS   300
SGSSQSSAHS QYNIQNISTG PRKNQIEIKL EPPQRNNSSK LRSSGPRTSS TSSSVNSQTL   360
NRNQPTVYIA ASPPNTDELM SRSQPKVYIS ANAATGDEQV MRNQPTLFIS TNSGASAASR   420
NMSGQVSMGP AFIHHHPPKS RAIGNNSATS PRVVVTQPNT KYTFKITVSP NKPPAVSPGV   480
VSPTFBLTNL LNHPDHYVET ENIQHLTDPT LAHVDRISET RKLSMGSDDA AYTQALLVHQ   540
KARMERLQRE LEIQKKRLDK LKSEVNEMEN NLTRRRLKRS NSISQIPSLE EMQQLRSCNR   600
QLQIDIDCLT KBIDLFQARG PHFNPSAIHN FYDNIGFVGP VPPKPKDQRS IIKTPKTQDT   660
EDDEGAQWNC TACTFLNHPA LIRCEQCEMP RHF                                693
```

FIG. 1A

```
         VII                                                                          VIII
TAK1  DFGTACDIQTHMTNNK----------------------------------                         GSAAWMAPE
                  *
MEKK1 DFGAAARLASKGTGAGEFQGQLL-------------------------                           GTIAFMAPE
                                                                                   *
MEKK2 DFGASKRLQTICLSGTGMKSVT--------------------------                           GTPYWMAPE

MEKK3 DFGASKRLQTICMSGTGIRSVT--------------------------                           GTPYWMAPE
                                                                                   *
SSK2  DFGAAKKIANNGTRLASMNKIENADGEHEDVTHVSD                                       GTPMYMAPE

MLK3  DFGLAREWHKTTQMSAA------------------------------   SKAVKNNENALLDMMG         GTYAWMAPE

ASK1  DFGTSKRLAGINPCTETFT----------------------------                            GTLQYMAPE

Raf1  DFGLATVKSRWSGSQQVEQPT---------------------------                           GSVLWMAPE

MTK1  DFGCSVKLTMPGEVNSTL-----------------------------                            GTAAYMAPE
                                                                                192
```

FIG. 6C

SIGNAL TRANSDUCTION PROTEIN TAB2

TECHNICAL FIELD

The present invention relates to a novel signal transduction protein involved in the signal transduction of proinflammatory cytokine IL-1. Also, the present invention relates to a method of screening for compounds that inhibit an activity of the protein. The present invention also relates to a pharmaceutical composition containing the inhibitory agent of the protein activity as active ingredient.

BACKGROUND

Interleukin-1 (IL-1) is a proinflammatory cytokine that has several effects in the inflammation process. Stimulation of cells with IL-1 initiates a cascade of signaling events, including activation of c-Jun N-terminal kinase (JNK) and of nuclear transcription factor κB (NF-κB), which up-regulates the expression of many proinflammatory genes in the nucleus (Dinarello, Blood 87:2095–2147, 1996). In unstimulated cells, NF-κB is sequestered in the cytoplasm in a complex with inhibitory proteins I κB. Following stimulation with cytokines and other extracellular stimuli, the I κB proteins are phosphorylated on specific serine residues, which trigger the ubiquitination and subsequent degradation of I κB through the proteasome pathway. Proteolysis of I κB release NF-κB to translocate into the nucleus, where it stimulates transcription of specific target genes (Thanos et al., Cell 80:529–532, 1995; Verma et al., Genes Dev. 9:2723–2735, 1995; Baeuerle et al. Cell 87:13–20, 1996).

Recent studies have provided a model for how the IL-1 signal transduction cascade is regulated. The first signaling event for IL-1 is a ligand-induced complex formation of the type I receptor (IL-1RI) and the receptor accessory protein (IL-1RAcP) (Greenfeder et al., J. Biol. Chem. 270:13757–13765, 1995; Huang et al., Proc. Natl. Acad. Sci. USA 94:12829-12832, 1997; Korherr et al., Eur. J. Immunol. 27:262–267, 1997; Wesche et al., J. Biol. Chem. 272: 7727–7731, 1997). The cytosolic myeloid differentiation protein MyD88 is next recruited to this complex (Cao et al., Science 271:1128–1131, 1996; Muzio et al., Science 278: 1612–1615, 1997; Wesche et al., Immunity 7:837–847, 1997; Bums et al., J. Biol. Chem. 273:12203–12209, 1998), which in turn enables the association of the serine/threonine IL-1 receptor-associated kinase (IRAK). IRAK becomes highly phosphorylated, leaves the receptor complex, and interacts with TRAF6 (TNF receptor-associated factor 6), which is required for IL-1-induced JNK and NF-κB activation (Cao et al., Nature 383:443–446, 1996; Yamin et al., J. Biol. Chem. 272:21540–21547, 1997; Lomaga et al., Genes Dev. 13:1015–1024, 1999). Another serine/threonine kinase, NF-κB -inducing kinase (NIK), is believed to be a downstream component in activating NF-κB, but not in the JNK activation, in response to IL-1 (Malinin et al., Nature 385: 540–544, 1997). Recently, two IκB kinases (IKKα/IKK1 and IKKβ/IKK2) have been implicated in signal-induced phosphorylation of the IκB proteins (DiDonato et al., Nature 388:548–554, 1997; Mercurio et al., Science 278:860–866, 1997; Regnier et al., Cell 90:373–383, 1997; Woronicz et al., Science 278:866–869, 1997; Zandi et al., Cell 91:243–252, 1997). The IKKs are components of a large complex, which contain NEMO (NF-κB essential modulator)/IKKγ (Rothwarf et al., Nature 395:297–300, 1998; Yamaoka et al., Cell 93:1231–1240, 1998). The present inventors have recently demonstrated that the protein kinase TAK1 is involved in the IL-1 signaling pathway (Ninomiya-Tsuji et al., Nature 398: 252–256, 1999). Following exposure of the cells to IL-1, endogenous TAK1 is recruited to the TRAF6 complex, where it becomes activated. Activated TAK1 then stimulates a MAP kinase cascade leading to JNK activation and a NIK-IKK cascade leading to NF-κB activation. Thus, TAK1 is positioned downstream of TRAF6 in the IL-1-activated signaling cascade. This suggests that the bifurcation of the IL-1-induced JNK and NF-κB activation pathways occurs at the level of TAK1.

TAK1 was originally identified as a MAP kinase kinase kinase (MAPKKK) that is activated by transforming growth factor-β (TGF-β) family ligands. The present inventors have previously demonstrated that TAK1 functions in TGF-β signaling pathways in mammalian cells (Yamaguchi et al., Science 270:2008–2011, 1995; Shibuya et al., Science 272: 1179–1182, 1996). In early *Xenopus* embryos TAK1 also participates in mesoderm induction and patterning meditated by bone morphogenetic protein (BMP), a TGF-β family ligand (Shibuya et al., EMBO J. 17:1019–1028, 1998; Yamaguchi et al., EMBO J. 18:179–187, 1999). Furthermore, the inventors have recently found that TAK1 is involved in the MAP kinase-like pathway that negatively regulates the Wnt signaling pathway (Ishitani et al., Nature 399:798–802, 1999). Thus, the fact that TAK1 has the capacity to activate distinct pathways raises the problem of how specificity in signaling pathways is achieved. The identification of specific components in different signaling pathways provides insight into the mechanisms for selective activation of TAK1 in response to divergent stimuli.

There are several groups of MAPKKKs including the Raf family (Raf-1 and B-Raf), the MEKK family (MEKK1, MEKK2, and MEKK3), the MLK family (MLK1, MLK2, MLK3, and DLK), as well as MTK1/MEKK4 and ASK1 (Fanger et al., Curr. Opin. Genet. Dev. 7:67–74, 1997; Robinson et al., Curr. Opin. Cell Biol. 9:180–186, 1997). Different mechanisms of MAPKKKs activation have been reported. Autophosphorylation mediated by an intra-molecular reaction has been implicated in the activation of MEKK1 and SSK2, a MAPKKK in budding yeast (Deak et al., Biochem. J. 322:185–192, 1997; Siow et al., J. Biol. Chem. 272:7586–7594, 1997; Posas et al., EMBO J. 17:1385–1394 1998). ASK1 and MLK3 have been demonstrated to form dimers in response to upstream stimuli, and this dimerization has been shown to be important for their catalytic activities (Gotoh et al., J. Biol. Chem., 273, 17477–17482, 1998; Leung et al., J. Biol. Chem. 273: 32408–32415, 1998). This dimerization may facilitate intermolecular autophosphorylation leading to activation, as is the case for receptor-tyrosine kinases. In some signaling pathways, MAPKKK kinases (MAPKKKKs) function upstream of MAPKKKs. For example, the Ste20 MAPKKKK in budding yeast functions to activate the Ste11 MAPKKK in the mating pheromone pathway (Herskowitz, Cell 80:187–197, 1995). Similarly, Ste20-like kinases are implicated in the activation of MAPKKKs in mammalian cells. Raf-1 is phosphorylated and activated by p21 (Rac/Cdc42)-activated kinase (PAK) (King et al., Nature 396: 180–183, 1998). Germinal center kinase (GCK) functions upstream of MEKK1 in the TNF-α signaling pathway leading to JNK activation. However, the molecular mechanism by which IL-1 activates TAK1 is yet to be elucidated.

SUMMARY

The present invention provides a novel signal transduction protein involved in the signal transduction of IL-1. Also, the present invention provides a method of screening for compounds that inhibit the signal transduction of IL-1 utilizing the protein. The present invention also provides an inhibitory agent of IL-1 signal transduction containing, as active ingredient, a compound isolated by the screening method.

The present inventors studied to find a novel protein binding to TAK1 in order to elucidate how IL-1 signal is integrated into lead to TAK1 activation. As a result, the inventors have identified a novel signal transducer "TAB2", which acts as an intermediary between TAK1 and TRAF6. An expression of TAB2 led to JNK and NF-κB activation, which are positioned downstream in the IL-1 signaling cascade. In addition, TAB2 dominant-negative mutant inhibited the activation mediated by IL-1. TAB2 translocated from membrane to cytoplasm by IL-1 stimuli, and mediated an association between TRAF6 and TAK1 depending on IL-1. Further, the inventors found that IL-1 activates TAK1 through autophosphorylation.

These results suggest that TAB2 functions as an adaptor linking TAK1 and TRAF6 and that TAB2 mediates TAK1 activation in the IL-1 signaling pathway. Since TAB2 has a function of IL-1 signal transduction to TAK1, it is possible to isolate a compound that regulates various biological reactions mediated by IL-1, by targeting for the signal transduction associated with TAB2 and screening for a compound regulating the signal transduction.

Also, it has been reported that TRAF6 is involved in signal transduction of IL-18 and LPS, as well as IL-1 (Clinical Immunology 32(3):269–276, 1999). TAB2 inhibitory agent can be used as therapeutic agent for inflammatory diseases and allergic diseases, due to the inhibitory effect against stimuli by IL-1, IL-18, LPS, and so on.

Especially, it is believed that although TAB2 mediates IL-1 signal transduction, TAB2 is not involved in TGF-β signal transduction pathway, which is another pathway in which TAK1 is involved. Therefore, the use of compounds that regulate signal transduction mediated by TAB2 makes it possible to specifically regulate biological reaction in response to IL-1 stimuli and to specifically treat or prevent diseases associated with IL-1. For example, an identification of a compound that inhibits binding between TAB2 and TAK1 or TRAF6 provides a novel approach for developing an inhibitory agent that inhibits IL-1 signal transduction. These inhibitory agents are important candidates for novel anti-inflammatory drug that has novel and ancillary function. In fact, the present inventors found that a partial peptide of TAB2 has an activity for inhibiting signal transduction from IL-1.

The present invention was carried out based on the above-mentioned findings, and provides a novel signal transduction protein TAB2, which is involved in IL-1 signal transduction. Also, the present invention provides a method of screening for inhibitory agents of IL-1 signal transduction mediated by TAB2. The present invention further provides an inhibitory agent of IL-1 signal transduction, where the agent contains, as active ingredient, a compound isolated by the screening method.

More specifically, the present invention provides:

1. a DNA encoding a protein or peptide that has binding activity to TAK1 and TRAF6, said DNA being selected from the group consisting of the following (a) to (e):
   (a) a DNA encoding a protein comprising an amino acid sequence set forth in SEQ ID NO:2;
   (b) a DNA comprising a coding region of a nucleotide sequence set forth in SEQ ID NO:1;
   (c) a DNA hybridizing with a DNA comprising a nucleotide sequence set forth in SEQ ID NO:1;
   (d) a DNA encoding a protein comprising an amino acid sequence set forth in SEQ ID NO:2 in which one or more amino acids have been substituted, deleted, inserted, and/or added; and
   (e) a DNA encoding a partial peptide of a protein comprising an amino acid sequence set forth in SEQ ID NO:2;

2. a DNA encoding a protein or peptide that has activity of signal transduction in response to IL-1 stimuli, said DNA being selected from the group consisting of the following (a) to (e):
   (a) a DNA encoding a protein comprising an amino acid sequence set forth in SEQ ID NO:2;
   (b) a DNA comprising a coding region of a nucleotide sequence set forth in SEQ ID NO:1;
   (c) a DNA hybridizing with a DNA comprising a nucleotide sequence set forth in SEQ ID NO:1;
   (d) a DNA encoding a protein comprising an amino acid sequence set forth in SEQ ID NO:2 in which one or more amino acids have been substituted, deleted, inserted, and/or added; and
   (e) a DNA encoding a partial peptide of a protein comprising an amino acid sequence set forth in SEQ ID NO:2;

3. a DNA encoding a protein or peptide that has binding activity to TAK1 or TRAF6, said DNA being selected from the group consisting of the following (a) and (b):
   (a) a DNA encoding a protein comprising an amino acid sequence set forth in SEQ ID NO:2 in which one or more amino acids have been substituted, deleted, inserted, and/or added; or
   (b) a DNA encoding a partial peptide of a protein comprising an amino acid sequence set forth in SEQ ID NO:2;

4. a DNA encoding a protein or peptide that has inhibitory activity of signal transduction in response to IL-1 stimuli, said DNA being selected from the group consisting of the following (a) and (b):
   (a) a DNA encoding a protein comprising an amino acid sequence set forth in SEQ ID NO:2 in which one or more amino acids have been substituted, deleted, inserted, and/or added; or
   (b) a DNA encoding a partial peptide of a protein comprising an amino acid sequence set forth in SEQ ID NO:2;

5. a protein or peptide encoded by the DNA according to any one of (1) to (4);

6. a vector into which the DNA according to any one of (1) to (4) has been inserted;

7. a host cell harboring the vector according to (6);

8. a method for producing the protein or peptide according to (5), comprising the steps of cultivating the host cell according to (7) and collecting, from said host cell or the culture supernatant thereof, the protein or peptide expressed;

9. an antibody that binds to the protein or peptide according to (5);

10. a polynucleotide comprising at least 15 nucleotides, which is complementary to a DNA comprising a nucleotide sequence set forth in SEQ ID NO:1 or the complementary strand thereof;

11. a method of screening for a compound that inhibits signal transduction of IL-1, comprising the steps of:
   (a) contacting a protein or peptide encoded by the DNA according to (1) or (3), with TAK1 protein and/or TRAF6 protein, in the presence of a test sample;

(b) detecting the binding between the protein or peptide encoded by the DNA according to (1) or (3), and TAK1 protein and/or TRAF6 protein; and
(c) selecting a compound that has activity for inhibiting the binding;
12. the method according to (11), wherein the detecting in step (b) is carried out by immunoprecipitation;
13. a method of screening for a compound that inhibits signal transduction of IL-1, comprising the steps of:
(a) contacting a mammalian cell that expresses a protein encoded by the DNA according to (2), with IL-1, in the presence of a test sample;
(b) detecting a biological activity that is transduced by the protein encoded by the DNA according to (2); and
(c) selecting a compound that decreases said biological activity;
14. the method according to (13), wherein the biological activity is an activation of TAK1;
15. the method according to (14), wherein the activation of TAK1 is detected by phosphorylation of MKK6;
16. the method according to (13), wherein the biological activity is an activation of NF-κB;
17. the method according to (16), wherein the activation of NF-κB is detected by introducing, into a cell, a vector comprising a reporter gene that binds to downstream of Ig-κ promoter, and detecting an expression of the reporter gene inside the cell;
18. the method according to (13), wherein the biological activity is an activation of JNK;
19. the method according to (18), wherein the activation of JNK is detected by phosphorylation of Jun;
20. the method according to (13), wherein the biological activity is translocation of a protein encoded by the DNA according to (2) from cell membrane to cytoplasm;
21. the method according to (13), wherein the biological activity is autophosphorylation of TAK1;
22. the method according to any one of (13) to (21), wherein the method uses a mammalian cell into which a vector expressing the DNA according to (2) has been introduced;
23. an inhibitory agent of IL-1 signal transduction, said agent comprising, as an active ingredient, a compound that is isolatable by the method according to any one of (11) to (22);
24. an inhibitory agent of IL-1 signal transduction, said agent comprising, as an active ingredient, a compound that inhibits the binding between a protein or peptide encoded by the DNA according to (1) and TAK1 protein and/or TRAF6 protein;
25. an inhibitory agent of signal transduction of IL-1, IL-18, or LPS, said agent comprising, as an active ingredient, the DNA according to (4), or a protein or peptide encoded by said DNA;
26. the inhibitory agent according to (25), wherein the peptide is TAB2-N or TAB2-C;
27. an inhibitory agent according to any one of (23) to (26), which is used to prevent or treat a disease or injury associated with inflammation; and
28. an anti-inflammatory agent or antiallergic agent comprising, as an active ingredient, a TAB2 inhibitory agent that is isolatable by the method according to (11) or (12).

In the present invention, the term "peptide" means a compound in which amino acids are bonded to each other by peptide bond. Accordingly, the inventive peptide also includes long chains of amino acids, namely, polypeptides and proteins.

The present invention provides a DNA encoding a novel signal transduction protein involved in signal transduction of IL-1. A cDNA nucleotide sequence from human TAB2 is represented in SEQ ID NO:1, and an amino acid sequence from the protein encoded by the cDNA is represented in SEQ ID NO:2, which have been isolated by this inventors. The protein acts as an adaptor molecule bridging TRAF6 and TAK1, and transduces signals of IL-1, which is a proinflammatory cytokine.

An isolated human TAB2 gene encodes a protein comprising 693 amino acids, which has no significant homology to known proteins except that it has structure expected to form amphipathic α-helix near C-terminus. It has been shown that TAB2 protein has an activity for binding to both of TRAF6 and TAK1 simultaneously, due to the complex formation, that TRAF6 signal is transduced to TAK1, and that, thus, autophosphorylation of TAK1 and activation of kinase activity occur. In addition, the expression of TAB2 led to activation of NF-κB and JNK, which are known to be downstream of IL-1 signal transduction. Also, it has been revealed that dominant negative mutant of TAB2 acts as a molecule that inhibits signal transduction in TAB2, and inhibits signal transduction by IL-1. These results show that TAB2 acts as an adaptor molecule of TRAF6 and TAK1 in signal transduction of IL-1.

Especially, although TAB2 mediates signal transduction of IL-1, it may be not involved in TGF-β signal transduction pathway, which is another signaling pathway in which TAK1 is involved. Therefore, TAB2 is an important target molecule for developing inhibitory agent specific to signal transduction of IL-1, and the inhibitory agent is an important candidate for developing a novel anti-inflammatory agent. A molecule that inhibits signal transduction in TAB2 is expectedly applied for preventing or treating various diseases or injury associated with inflammation.

The present invention also encompasses proteins (or peptides) functionally equivalent to human TAB2 proteins (SEQ ID NO:2). Such proteins include, for example, homologous proteins derived from other organisms corresponding to the human "TAB2" protein, as well as mutants of human TAB2 proteins. In the present invention, the term "functionally equivalent" means that the subject protein has binding activity to TRAF6 and TAK1, and acts as an adaptor molecule for these proteins in signal transduction in response to IL-1 stimuli.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

Accordingly, the invention includes a polypeptide having a sequence shown as SEQ ID NO:2. The invention also includes a polypeptide, or fragment thereof, that differs from the corresponding sequence shown as SEQ ID NO:2. The differences are, preferably, differences or changes at a non-essential residue or a conservative substitution. In one embodiment, the polypeptide includes an amino acid sequence at least about 60% identical to a sequence shown as SEQ ID NO:2, or a fragment thereof. Preferably, the polypeptide is at least 65%, 70%, 75%, 80%, 85%, 90%, 95%, 98%, 99% or more identical to SEQ ID NO:2 and has at least one TAB2 function or activity described herein, e.g., binding to TRAF6 or TAK1. Preferred polypeptide fragments of the invention are at least 10%, preferably at least 20%, 30%, 40%, 50%, 60%, 70%, or more, of the length of the sequence shown as SEQ ID NO:2 and have at least one TAB2 function or activity described herein. Or alternatively, the fragment can be merely an immunogenic fragment.

Methods for preparing proteins functionally equivalent to a given protein are well known by a person skilled in the art and include known methods of introducing mutations into the protein. For example, one skilled in the art can prepare proteins functionally equivalent to the human TAB2 protein by introducing an appropriate mutation in the amino acid sequence of the human "TAB2" protein (SEQ ID NO:2) by site-directed mutagenesis (Hashimoto-Gotoh et al. Gene 152:271–275, 1995; Zoller et al., Methods Enzymol. 100: 468–500, 1983; Kramer et al., Nucleic Acids Res. 12:9441–9456, 1984; Kramer et al., Methods. Enzymol. 154:350–367, 1987; Kunkel, Proc. Natl. Acad. Sci. USA 82:488–492, 1985; Kunkel, Methods Enzymol. 85:2763–2766, 1988), etc. Amino acid mutations can also occur in nature. Thus, the protein of the present invention includes those proteins having the amino acid sequences of the human "TAB2" protein (SEQ ID NO:2) in which one or more amino acids are mutated, provided the resulting mutated proteins are functionally equivalent to the human TAB2 protein. The number of amino acids to be mutated in such a mutant may be generally 100 amino acids or less, preferably 50 amino acids or less, more preferably 20 amino acids or less, more preferably 10 amino acids or less, more preferably 5 amino acids or less, and more preferably 3 amino acids or less.

The amino acid residue to be mutated is preferably mutated into a different amino acid in which the properties of the amino acid side-chain are conserved. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W) (The parenthetic letters indicate the one-letter codes of amino acids).

Mutated or modified proteins, proteins having amino acid sequences modified by deleting, adding, and/or replacing one or more amino acid residues of a certain amino acid sequence, have been known to retain the original biological activity (Mark et al., Proc. Natl. Acad. Sci. USA 81:5662–5666, 1984; Zoller et al., Nucleic Acids Res. 10:6487–6500, 1982; Wang et al., Science 224:1431–1433; Dalbadie-McFarland et al., Proc. Natl. Acad. Sci. USA 79:6409–6413, 1982).

A protein to which plural amino acids are added to the amino acid sequence of human "TAB2" protein encompasses a fusion protein containing the human "TAB2" protein. Fusion proteins are fusions of the human "TAB2" protein and other peptides or proteins, and are included in the present invention. Fusion proteins can be made by techniques well known to a person skilled in the art, such as by linking the DNA encoding the human "TAB2" protein (SEQ ID NO:2) with DNA encoding other peptides or proteins, so that the frames match, inserting the fusion DNA into an expression vector, and expressing it in a host. There is no restriction on the peptides or proteins fused to the protein of the present invention.

Known peptides that can be used as peptides that are fused to the protein of the present invention include, for example, FLAG (Hopp et al., Biotechnology 6:1204–1210, 1986), 6×His containing six His (histidine) residues, 10×His, HA (Influenza agglutinin), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that are fused to a protein of the invention include GST (glutathione-S-transferase), HA (Influenza agglutinin), immunoglobulin constant region, β-galactosidase, MBP (maltose-binding protein), and such.

Fusion proteins can be prepared by fusing commercially available DNA encoding the peptides or proteins discussed above, with the DNA encoding the protein of the present invention and expressing the fused DNA prepared.

An alternative method well known in the art to prepare a protein functionally equivalent to a given protein is, for example, the method using a hybridization technique (Sambrook, et al., Molecular Cloning 2nd ed. 9.47–9.58, Cold Spring Harbor Lab. Press, 1989). One skilled in the art can readily isolate a DNA having high homology with a whole or part of the DNA sequence (SEQ ID NO:1) encoding the human "TAB2" protein, and isolate functionally equivalent proteins to the human "TAB2" protein from the isolated DNA. The proteins of the present invention include those that are encoded by DNA that hybridize with the DNA encoding the human "TAB2" protein under stringent conditions and are functionally equivalent to the human "TAB2" protein. These proteins include mammal homologues protein derived from non-human mammals (for example, a protein encoded by a mouse, monkey, rat, rabbit, bovine, porcine, dog, and cat gene). In isolating a cDNA highly homologous to the DNA encoding the human "TAB2" protein from animals, it may be preferable to use tissues such as spleen, thymus, heart, ovary, testis, kidney, liver, and the like.

The hybridization condition for isolating a DNA encoding a protein functionally equivalent to the human "TAB2" protein can be selected appropriately by a person skilled in the art. An example of hybridization conditions includes low stringent conditions. A low stringent condition is, for example, washing in 42° C., 5×SSC, 0.1% sodium dodecyl sulfate, 50% formamide. More preferably, high stringent conditions are used. A high stringent condition is, for example, washing in 0.1×SSC, 0.1% sodium dodecyl sulfate at 60° C. It has already been known that a protein which is encoded by a DNA hybridizing to a nucleotide sequence encoding a given protein under suitable stringent conditions, has the same biological activity as the given protein. Under these conditions, the higher the temperature, the higher the homology of the obtained DNA will be. However, several factors such as temperature and salt concentration can influence the stringency of hybridization and one skilled in the art can suitably select the factors to achieve the similar stringency.

In place of hybridization, a gene amplification method, for example, the polymerase chain reaction (PCR) method, can be utilized to isolate a DNA encoding a protein functionally equivalent to the human "TAB2" protein, using a primer synthesized based on the sequence information of the DNA (SEQ ID NO:1) encoding the human "TAB2" protein.

Proteins that are functionally equivalent to the human "TAB2" protein encoded by the DNA isolated through the above hybridization techniques or gene amplification techniques, normally have a high homology to the amino acid sequence of the human "TAB2" protein (SEQ ID NO:2). The protein of the present invention also encompasses a protein that is functionally equivalent to human "TAB2" protein and that has high homology to the amino acid sequence set forth in SEQ ID NO:2. High homology refers to a sequence identity of typically 60% or higher, preferably 80% or higher, more preferably 90% or higher, even more preferably 95% or higher (for example, 98% or higher). The homology of a protein can be determined by following the algorithm in "Wilbur, W. J. and Lipman, D. J., Proc. Natl. Acad. Sci. USA (1983) 80, 726–730".

Also, the present invention encompasses a mutant or partial peptide of TAB2 protein that has binding activity to TRAF6 and TAK1, and that has activity for inhibiting signal transduction in response to IL-1 sitmuli. An example of these peptides is N-terminal peptide of TAB2 protein (see Example 2). In addition, the present invention encompasses a mutant or partial peptide of TAB2 protein that has binding activity to either TRAF6 or TAK1. These proteins and peptides may have the activity to compete with endogenous TAB2 protein and inhibit signal transduction in response to IL-1 stimuli. The present invention also encompasses a mutant and partial peptide of TAB2 protein that binds to neither TRAF6 nor TAK1 and that has activity for inhibiting signal transduction in response to IL-1 stimuli. These proteins and peptides are important candidates for drugs for treating or preventing diseases associated with inflammation.

A protein of the present invention may have variations in amino acid sequence, molecular weight, isoelectric point, the presence or absence of sugar chains, the position of added sugar chains, the structure of sugar chains, the state of phosphorylation, and/or the presence or absence of disulfide bond, depending on the cell or host used to produce it or the purification method utilized as described later. Nevertheless, so long as the obtained protein has a function equivalent to that of the human "TAB2" protein, it is within the scope of the present invention. For example, when the inventive protein is expressed in prokaryotic cells, e.g., *Escherichia coli*, a methionine residue is added at the N-terminus in the amino acid sequence of the original protein. The present invention also includes such proteins.

The proteins of the present invention can be prepared as recombinant proteins or natural proteins, by methods well known to those skilled in the art. A recombinant protein can be prepared by inserting a DNA, which encodes the protein of the present invention (for example, the DNA comprising the nucleotide sequence of SEQ ID NO:1), into an appropriate expression vector, introducing the vector into an appropriate host cell, collecting thus obtained recombinants, obtaining the extract thereof, and purifying the protein by subjecting the extract to chromatography, for example, ion exchange chromatography, reverse-phase chromatography, gel filtration, or affinity chromatography utilizing a column to which antibodies against the protein of the present invention is fixed, or by combining more than one of aforementioned columns.

Also when the protein of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein from the fusion protein by cutting with thrombin, factor-Xa, or the like as required.

A natural protein can be isolated by methods known to a person skilled in the art, for example, by contacting the affinity column, in which antibodies binding to the protein of the present invention described below are bound, with the extract of tissues or cells expressing the protein of the present invention. The antibodies can be polyclonal antibodies or monoclonal antibodies.

The present invention also encompasses partial peptides of the protein of the present invention. The inventive partial peptide consists of an amino acid sequence comprising at least 7 amino acids or more, preferably 8 amino acids or more, and more preferably 9 amino acids or more. In addition to the use as inhibitor of signal transduction of IL-1 as described above, the partial peptide can be used, for example, for preparing antibodies against the protein of the present invention, screening for an inhibitory agent of binding between the inventive protein and TAK1 or TRAF6, and so on. A partial peptide of the invention can be produced by genetic engineering, by known methods of peptide synthesis, or by digesting the protein of the invention with an appropriate peptidase. For peptide synthesis, for example, solid phase synthesis or liquid phase synthesis may be used.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated or purified nucleic acid molecule that encodes a polypeptide described herein or a fragment thereof. Preferably, the isolated nucleic acid molecule includes a nucleotide sequence that is at least 60% identical to the nucleotide sequence shown in SEQ ID NO:1. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1. In the case of an isolated nucleic acid molecule which is longer than or equivalent in length to the reference sequence, e.g., SEQ ID NO:1, the comparison is made with the full length of the reference sequence. Where the isolated nucleic acid molecule is shorter than the reference sequence, e.g., shorter than SEQ ID NO:1, the comparison is made to a segment of the reference sequence of the same length (excluding any loop required by the homology calculation).

As used herein, "% identity" of two amino acid sequences, or of two nucleic acid sequences, is determined using the algorithm of Karlin and Altschul (Proc. Natl. Acad. Sci. USA 87:2264–2268, 1990), modified as in Karlin and Altschul, Proc. Natl. Acad. Sci. USA 90:5873–5877, 1993). Such an algorithm is incorporated into the NBLAST and XBLAST programs of Altschul et al. (J. Mol. Biol. 215: 403–410, 1990). BLAST nucleotide searches are performed with the NBLAST program, score=100, wordlength=12. BLAST protein searches are performed with the XBLAST program, score=50, wordlength=3. To obtain gapped alignment for comparison purposes, GappedBLAST is utilized as described in Altschul et al (Nucleic Acids Res. 25:3389–3402, 1997). When utilizing BLAST and Gapped-BLAST programs the default parameters of the respective programs (e.g., XBLAST and NBLAST) are used to obtain nucleotide sequences homologous to a nucleic acid molecule of the invention.

The DNA encoding the protein of the present invention can be used for the in vivo or in vitro production of the protein of the present invention as described above, and can be applied to gene therapy for diseases attributed to genetic abnormality in the gene encoding the protein of the present invention and diseases that are treatable with the protein of the present invention. Any form of the DNA of the present invention can be used, so long as it encodes the protein of the present invention. Specifically, cDNA synthesized from the mRNA, genomic DNA, and chemically synthesized DNA can be used. The DNA of the present invention includes a DNA comprising a given nucleotide sequences based on degeneration of its genetic codes, so long as the resulting DNA encodes a protein of the present invention.

The DNA of the present invention can be prepared by methods known to a person skilled in the art. For example, the DNA of the present invention can be prepared by: preparing a cDNA library from cells which express the protein of the present invention, and conducting hybridization using a partial sequence of the DNA of the present invention (for example, SEQ ID NO:1) as a probe. A cDNA library can be prepared, for example, by the method described in Sambrook et al., Molecular Cloning, Cold Spring Harbor Laboratory Press, 1989); alternatively, commercially available DNA libraries may be used. A cDNA library can be also prepared by: extracting RNAs from cells expressing the protein of the present invention, synthesizing cDNAs with reverse transcriptase, synthesizing oligo DNAs based on the sequence of the DNA of the present invention (for example, SEQ ID NO:1), conducting PCR by using the oligos as primers, and amplifying cDNAs encoding the protein of the present invention.

In addition, by sequencing the nucleotides of the obtained cDNA, the translation region encoded by the cDNA can be determined, and the amino acid sequence of the protein of the present invention can be obtained. Moreover, by screening the genomic DNA library using the obtained cDNA as a probe, the genomic DNA can be isolated.

More specifically, mRNAs may first be prepared from cells, tissue, or organ (for example, blood cells such as leukocytes, or tissues such as spleen, liver, and kidney) in which the protein of the invention is expressed. Known methods can be used to isolate mRNAs; for instance, total RNA may be prepared by guanidine ultracentrifugation (Chirgwin et al., Biochemistry 18:5294–5299, 1979) or AGPC method (Chomczynski et al., Anal. Biochem. 162: 156–159, 1987). In addition, mRNA may be purified from total RNA using MRNA Purification Kit (Pharmacia) and such or, alternatively, mRNA may be directly purified by QuickPrep mRNA Purification Kit (Pharmacia).

The obtained mRNA is used to synthesize cDNA using reverse transcriptase. cDNA may be synthesized by using a commercially available kit, such as the AMV Reverse Transcriptase First-strand cDNA Synthesis Kit (Seikagaku Kogyo). Alternatively, cDNA may be synthesized and amplified following the 5'-RACE method (Frohman et al., Proc. Natl. Acad. Sci. USA 85:8998–9002, 1988; Belyavsky et al., Nucleic Acids Res. 17:2919–2932, 1989), which uses a primer and such, described herein, the Marathon DNA Amplification Kit (Clontech), and polymerase chain reaction (PCR).

A desired DNA fragment is prepared from the PCR products and ligated with a vector DNA. The recombinant vectors are used to transform *E. Coli* and such, and a desired recombinant vector is prepared from a selected colony. The nucleotide sequence of the desired DNA can be verified by conventional methods, such as dideoxynucleotide chain termination.

The nucleotide sequence of a DNA of the invention may be designed to be expressed more efficiently by taking into account the frequency of codon usage in the host to be used for expression (Grantham et al., Nucleic Acids Res. 9:43–74, 1981). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of the initiation codon (ATG) and/or the stop codon (TAA, TGA, or TAG).

Specifically, the DNA of the present invention encompasses the DNA comprising the nucleotide sequence from base A at position 81 to base C at position 2159 of SEQ ID NO:1.

Furthermore, the present invention includes a DNA that hybridizes with a DNA having a nucleotide sequence of SEQ ID NO:1, and that encodes a protein functionally equivalent to the protein of the invention described above. One skilled in the art may appropriately choose the conditions of hybridization. Specifically, the same condition as those described above can be used. Under these conditions, the higher the temperature, the higher the homology of the obtained DNA will be. The hybridizing DNA above is preferably a natural DNA, for example, a cDNA or a chromosomal DNA.

The present invention also provides a vector into which a DNA of the present invention is inserted. A vector of the present invention is useful to keep a DNA of the present invention in a host cell, or to express the protein of the present invention.

When *E. coli* is a host cell and the vector is amplified and produced in a large amount in *E. coli* (e.g., JM109, DH5α, HB101, or XL1Blue), there is no restriction on the vector, so long as it has "ori" to be amplified in *E. Coli* and a marker gene for selecting transformed *E. coli* (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT, and pT7 can also be used for subcloning and extracting cDNA as well as the vectors described above. When a vector is used to produce the protein of the present invention, an expression vector is especially useful. For example, an expression vector to be expressed in *E. coli* should have the above characteristics to be amplified in *E. Coli*. When *E. coli*, such as JM109, DH5α, HB101, or XL1 Blue, are used as a host cell, the vector should have a promoter, for example, lacZ promoter (Ward et al., Nature 341:544–546, 1989; FASEB J. 6:2422–2427, 1992), araB promoter (Better et al., Science 240:1041–1043, 1988), or T7 promoter or the like, that can efficiently express the desired gene in *E. coli*. In that respect, pGEX-5X-1 (Pharmacia), "QIAEXPRESS system" (Qiagen), pEGFP and pET (in this case, the host is preferably BL21 which expresses T7 RNA polymerase), for example, can be used instead of the above vectors.

Additionally, the vector may also contain a signal sequence for polypeptide secretion. An exemplary signal sequence that directs the protein to be secreted to the periplasm of the *E. coli* is the pelB signal sequence (Lei et al., J. Bacteriol. 169:4379, 1987). Means for introducing the vectors into the target host cells include, for example, the calcium chloride method, and the electroporation method.

In addition to *E. Coli*, for example, expression vectors derived from mammals (for example, pcDNA3 (Invitrogen) and pEGF-BOS (Nucleic Acids. Res. 1990, 18 (17), p5322), pEF, pCDM8), expression vectors derived from insect cells (for example, "BAC-TO-BAC baculovirus expression system" (GIBCO BRL), pBacPAK8), expression vectors derived from plants (for example pMH1, pMH2), expression vectors derived from animal viruses (for example, pHSV, pMV, pAdexLcw), expression vectors derived from retroviruses (for example, pZIpneo), expression vector derived from yeast (for example, "Pichia Expression Kit" (Invitrogen), pNV11, SP-Q01), and expression vectors derived from *Bacillus subtilis* (for example, pPL608, pKTH50) can be used for producing the protein of the present invention.

In order to express the vector in animal cells, such as CHO, COS, or NIH3T3 cells, the vector should have a promoter necessary for expression in such cells, for example, the SV40 promoter (Mulligan et al., Nature 277: 108, 1979), the MMLV-LTR promoter, the EF1α promoter (Mizushima et al., Nucleic Acids Res. 18:5322, 1990), the CMV promoter, and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV, and pOP13.

In addition, methods may be used to express a gene stably and, at the same time, to amplify the copy number of the gene in cells. For example, a vector comprising the complementary DHFR gene (for example pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transfected into COS cells comprising the SV40 T antigen expressing gene on the chromosome can be used. Examples of replication origins to be used in the present invention include those derived from polyomavirus, adenovirus, bovine papilomavirus (BPV), and such. Moreover, to amplify the gene copies in host cell lines, the expression vector may include an aminoglycoside transferase (APH) gene, thymidine kinase (TK) gene, *E. coli* xanthine guanine phosphoribosyl transferase (Ecogpt) gene, dihydrofolate reductase (dhfr) gene, and such as a selective marker.

The DNA of the present invention can further be expressed in vivo in animals, for example, by inserting the DNA of the present invention into an appropriate vector and introducing it into living bodies by methods such as the retrovirus method, the liposome method, the cationic liposome method, and the adenovirus method. In such a manner, gene therapy against diseases attributed to mutation of "YS68" gene of the present invention can be accomplished. As a vector to be used, for example, adenovirus vector (for example pAdexlcw), and retrovirus vector (for example, pZIPneo) can be mentioned, but is not restricted thereto. General gene manipulation, such as insertion of the DNA of the present invention to a vector, can be performed according to conventional methods (Molecular Cloning, 5. 61–5. 63). Administration into a living body can be either an ex vivo method, or in vivo method.

The present invention further provides a host cell into which the vector of the present invention has been transfected. The host cell into which the vector of the invention is transfected is not particularly limited. For example, *E. coli*, various animal cells and such can be used. The host cells of the present invention can be used, for example, as a production system for producing or expressing the protein of the present invention. The present invention provides methods of producing a protein of the invention both in vitro and in vivo. For in vitro production, eukaryotic cells or prokaryotic cells can be used as host cells.

Useful eukaryotic cells may be animal plant, or fungi cells. Exemplary animal cells include, for example, mammalian cells such as CHO (J. Exp. Med. 108:945, 1995), COS, 3T3, myeloma, baby hamster kidney (BHK), HeLa, or Vero cells, amphibian cells such as *Xenopus* oocytes (Valle et al., Nature 291:340–358, 1981), or insect cells such as Sf9, Sf21, or Tn5 cells. CHO cells lacking DHFR gene (dhfr-CHO) (Proc. Natl. Acad. Sci. USA 77:4216–4220, 1980) or CHO K-1 (Proc. Natl. Acad. Sci. USA 60:1275, 1968) may also be used. Of the animal cells, CHO cells are particularly preferable for the mass expression. A vector can be transfected into host cells by, for example, the calcium phosphate method, the DEAE-dextran method, the cationic liposome DOTAP (Boehringer Mannheim), the electroporation method, the lipofection method, and so on.

As plant cells, plant cells originating from *Nicotiana tabacum* are known as protein-production systems, and may be used as callus cultures. As fungi cells, yeast cells such as *Saccharomyces*, including *Saccharomyces cerevisiae*, or filamentous fungi such as *Aspergillus*, including *Aspergillus niger*, are known and may be used herein.

Useful prokaryotic cells include bacterial cells, such as *E. coli*, for example, JM109, DH5α, and HB101. Other bacterial systems include, *Bacillus subtilis*.

These cells are transformed by a desired DNA, and the resulting transformants are cultured in vitro to obtain the protein. Transformants can be cultured using known methods. Culture medium for animal cells include, for example, DMEM, MEM, RPMI1640, or IMDM may be used with or without serum supplement such as fetal calf serum (FCS). The pH of the culture medium is preferably between about 6 and 8. Such cells are typically cultured at about 30 to 40° C. for about 15 to 200 hr, and the culture medium may be replaced, aerated, or stirred if necessary.

Examples of systems for producing the protein in vivo include production systems using animals and production system using plants. A desired DNA can be transfected into an animal or plant host. Encoded proteins are produced in vivo, and then recovered. These animal and plant hosts are included in host cells of the present invention.

Animals to be used for the production system described above include, but are not limited to, mammals and insects. Mammals, such as goat, porcine, sheep, mouse, and bovine, may be used (Vicki Glaser, SPECTRUM Biotechnology Applications (1993)). Alternatively, the mammals may be transgenic animals.

For instance, a desired DNA may be prepared as a fusion gene, by fusing it with a gene, such as goat β casein gene which encodes a protein specifically produced into milk. DNA fragments comprising the fusion gene are injected into goat embryos, which are then impregnated into female goats. Proteins are recovered from milk produced by the transgenic goats (i.e., those born from the goats that had received the modified embryos) or from their offspring. To increase the amount of milk containing the proteins produced by transgenic goats, appropriate hormones may be administered to them (Ebert et al., Bio/Technology 12:699–702, 1994).

Alternatively, insects, such as the silkworm, may be used. A DNA encoding a desired protein inserted into baculovirus can be used to transfect silkworms, and the desired protein may be recovered from their body fluid (Susumu et al., Nature 315:592–594, 1985).

As plants, for example, tobacco can be used. In use of tobacco, a DNA encoding a desired protein may be inserted into a plant expression vector, such as pMON530, which is introduced into bacteria, such as *Agrobacterium tumefaciens*. Then, the bacteria is used to transfect a tobacco plant, such as *Nicotiana tabacum*, and a desired polypeptide is recovered from their leaves (Julian et al., Eur. J. Immunol. 24:131–138, 1994).

A protein of the present invention obtained as above may be isolated from inside or outside (such as medium) of host cells, and purified as a substantially pure homogeneous protein. The method for protein isolation and purification is not limited to any specific method; in fact, any standard method may be used. For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press, 1996). These chromatographies may be performed by liquid chromatography, such as HPLC and FPLC. Thus, the present invention provides for highly purified proteins prepared by the above methods.

A protein of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase, and so on.

The present invention provides an antibody that binds to the protein of the invention. The antibody of the invention can be used in any form, such as monoclonal or polyclonal antibodies, and includes antiserum obtained by immunizing an animal such as a rabbit with the protein of the invention, all classes of polyclonal and monoclonal antibodies, human antibodies, and humanized antibodies produced by genetic recombination.

A protein of the invention used as an antigen to obtain an antibody may be derived from any animal species, but preferably is derived from a mammal such as a human, mouse, or rat, more preferably from a human. A human-derived protein may be obtained from the nucleotide or amino acid sequences disclosed herein.

According to the present invention, the protein to be used as an immunization antigen may be a complete protein or a partial peptide of the protein. A partial peptide may comprise, for example, the amino (N)-terminal or carboxy (C)-terminal fragment of a protein of the present invention. Herein, an antibody is defined as a protein that reacts with either the full length or a fragment of a protein of the present invention.

A gene encoding a protein of the invention or its fragment may be inserted into a known expression vector, which is then used to transform a host cell as described herein. The desired protein or its fragment may be recovered from the outside or inside of host cells by any standard method, and may subsequently be used as an antigen. Alternatively, cells expressing the protein or their lysates, or a chemically synthesized protein of the present invention may be used as the antigen. A short peptide that is bound appropriately with a carrier protein such as keyhole limpet hemocyanin, bovine serum albumin, and ovalbumin, is used preferably as an antigen.

Any mammalian animal may be immunized with the antigen, but preferably the compatibility with parental cells used for cell fusion is taken into account. In general, animals of Rodentia, Lagomorpha, or Primates are used.

Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, sacred baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the proteins of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the protein of the present invention using, for example, an affinity column coupled with the protein of the present invention, and farther purifying this fraction by using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre et al., Methods Enzymol. 73:3–46, 1981).

Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method in which a non-human animal is immunized with an antigen for preparing hybridoma, a hybridoma producing a desired human antibody that is able to bind to the protein can be obtained by the following method. First, human lymphocytes such as those infected by EB virus may be immunized with a protein, protein expressing cells, or their lysates in vitro. Then, the immunized lymphocytes are fused with human-derived myeloma cells that are capable of indefinitely dividing, such as U266, to yield the desired hybridoma (Unexamined Published Japanese Patent Application No. (JP-A) Sho 63-17688).

The obtained hybridomas are subsequently transplanted into the abdominal cavity of a mouse and the ascites are harvested. The obtained monoclonal antibodies can be purified by, for example, ammonium sulfate precipitation, a protein A or protein G column, DEAE ion exchange chromatography, or an affinity column to which the protein of the present invention is coupled. The antibody of the present invention can be used not only for purification and detection of the protein of the present invention, but also as a candidate for agonists and antagonists of the protein of the present invention. In addition, this antibody can be applied to the antibody treatment for diseases related to the protein of the present invention. When the obtained antibody is to be administered to the human body (antibody treatment), a human antibody or a humanized antibody is preferable for reducing immunogenicity.

For example, transgenic animals having a repertory of human antibody genes may be immunized with an antigen selected from a protein, protein expressing cells, or their lysates. Antibody producing cells are then collected from the animals and fused with myeloma cells to obtain hybridoma, from which human antibodies against the protein can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck C. A. K. and Larrick J. W. Therapeutic Monoclonal Antibodies, published in the United Kingdom by MacMillan Publishers LTD, 1990). A DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the proteins of the invention. For instance, the antibody fragment may be Fab, F(ab')$_2$, Fv, or single chain Fv (scFv), in which Fv fragments from H and L chains are ligated by an appropriate linker (Huston et al., Proc. Natl. Acad. Sci. USA 85:5879–5883, 1988). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co et al., J. Immunol. 152:2968–2976, 1994; Better et al., Methods Enzymol. 178:476–496, 1989; Pluckthun et al., Methods Enzymol. 178:497–515, 1989; Lamoyi, Methods Enzymol. 121:652–663, 1986; Rousseaux et al., Methods Enzymol. 121:663–669, 1986; Bird et al., Trends Biotechnol. 9:132–137, 1991).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but are not limited thereto. The concentration of the antibodies obtained as above may be determined by the measurement of absorbance, Enzyme-linked immunosorbent assay (ELISA), or so on.

A protein A column and protein G column can be used as the affinity column. Exemplary protein A columns to be used include, for example, Hyper D, POROS, and Sepharose F.F. (Pharmacia).

Exemplary chromatography, with the exception of affinity includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography, such as HPLC, FPLC.

For example, measurement of absorbance, enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment may be used in this method. BIAcore (Pharmacia) may be used to evaluate the activity of the antibody according to the present invention.

The above methods allow for the detection or measurement of the protein of the invention, by exposing the antibody of the invention to a sample assumed to contain the protein of the invention, and detecting or measuring the immune complex formed by the antibody and the protein. Because the method of detection or measurement of the protein according to the invention can specifically detect or measure a protein, the method may be useful in a variety of experiments in which the protein is used.

The present invention also provides a polynucleotide comprising at least 15 nucleotides that is complementary to the DNA encoding the human "TAB2" protein (SEQ ID NO:1) or the complementary strand thereof.

Herein, the term "complimentary strand" is defined as one strand of a double strand DNA composed of A:T and G:C base pairs to the other strand. Also, "complimentary" is defined as not only those completely matching within a continuous region of at least 15 nucleotides, but also having a homology of at least 70% or more, preferably 80% or more, more preferably 90% or more, and even more preferably 95% or more within that region. The homology may be determined using the algorithm described herein.

Such nucleic acids include probes and primers that are used to detect or amplify the DNA encoding the protein of the present invention, as well as nucleotides and nucleotide derivatives (for example, antisense oligonucleotides, ribozymes, or the DNA coding them) that are used to suppress the expression of the protein of the present invention. Moreover, such nucleic acids can be utilized for the preparation of DNA chip.

When used as a primer, such a nucleic acid is complementary at the 3'-end, and restriction enzyme recognition sequences or tags can be added to the 5'-end.

The antisense oligonucleotide includes, for example, those hybridize with any site within the nucleotide sequence of SEQ ID NO:1. This antisense oligonucleotide is preferably against at least 15 continuous nucleotides of the nucleotide sequence of SEQ ID NO:1. The above-mentioned antisense oligonucleotide, which contains an initiation codon in the at least 15 continuous nucleotides, is even more preferred.

Derivatives or modified products of antisense oligonucleotides can be used as antisense oligonucleotides. Examples of such modified products include lower alkyl phosphonate modifications such as methyl-phosphonate-type or ethyl-phosphonate-type, phosphorothioate modifications and phosphoroamidate modifications.

The antisense oligonucleotides means, not only those in which the nucleotides corresponding to those constituting a specified region of a DNA or mRNA are entirely complementary, but also those having a mismatch of one or more nucleotides, as long as the DNA or mRNA and the antisense oligonucleotide can specifically hybridize with the nucleotide sequence of SEQ ID NO:1.

The antisense oligonucleotide derivatives of the present invention act upon cells producing the protein of the invention by binding to the DNA or mRNA encoding the protein, inhibiting its transcription or translation, promoting the degradation of the mRNA, and inhibiting the expression of the protein of the invention, thereby resulting in the inhibition of the protein's function.

An antisense oligonucleotide derivative of the present invention can be made into an external preparation, such as a liniment or a poultice, by mixing with a suitable base material which is inactive against the derivatives.

Also, as needed, the derivatives can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following usual methods.

The antisense oligonucleotide derivative of the present invention is given to the patient by directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The antisense oligonucleotide of the present invention inhibits the expression of the protein of the invention and is thereby useful for suppressing the biological activity of the protein of the present invention. Also, expression-inhibitory agents, comprising the antisense oligonucleotide of the present invention, are useful in the point that they can inhibit the biological activity of the protein of the present invention.

In addition, the present invention provides a screening method for compounds that inhibit the signal transduction of IL-1 by using TAB2. One embodiment of the screening method of the present invention is that in which the inhibition of the binding activity between TAB2 and TAK1 and/or TRAF6 is used as index. Compounds to be targeted for screening, include those which inhibit binding between TRAF6 and TAB2, those which inhibit binding between TAK1 and TAB2, and those which inhibit complexation of TRAF6, TAB2, and TAK1.

The screening method for such compounds comprises the following steps of:
 (a) contacting TAB2 protein with TAK1 protein and/or TRAF6 protein in the presence of a test sample;
 (b) detecting the binding between TAB2 protein and TAK1 protein and/or TRAF6 protein; and
 (c) selecting a compound having an activity for inhibiting the binding.

There is no restriction on test samples, and, for example, cell culture supernatant, products of fermenting microorganism, extracts from marine organism, plant extracts, prokaryotic cell extracts, eukaryotic single cell extracts, or animal cell extracts, or library thereof, purified or crude proteins, peptides, non-peptide compounds, synthetic micromolecular compounds and natural compounds, can be used. The protein of the present invention to be contacted with a test sample can be, for example, a purified protein, a soluble protein, a form bound to a carrier, a fusion protein fused with other proteins, a form expressed on the cell membrane, or membrane fraction.

There is no restriction on the form of the protein used for screening as above, so long as it has ability of binding or complexation. Such a protein can be, instead of full-length protein, a mutant or partial peptide. Alternatively, it may be a fusion protein with another peptide. TAB2 protein can be, for example, a protein that loses the function as an adaptor protein (or that is activated constantly), where the intact protein has the function, as well as full-length human TAB2 protein set forth in SEQ ID NO:2. For instance, it was shown that the partial peptide of C-terminal side comprising amino acids at 401 to 693 of human TAB2 protein binds to TRAF6 and TAK1. Therefore, using such TAB2 partial peptide, it is possible to screen for a compound that inhibits the binding with TRAF6 or TAK1. TRAF6 protein and/or TAK1 protein can be also a partial peptide or mutant protein that has lost its ability of signal transduction (or that is activated constantly), as well as full-length protein.

A method for generating such proteins as recombinant proteins can be conducted, specifically, in the following manner. The gene encoding the desired protein is expressed in animal cells and so on by inserting the gene to an expression vector for foreign genes, such as pSV2neo, pcDNA I, and pCD8. The promoter to be used for the expression may be any promoter that can be used commonly and include, for example, the SV40 early promoter (Rigby in Williamson (ed.), Genetic Engineering, vol. 3. Academic Press, London, p. 83–141, 1982), the EF-1α promoter (Kim et al., Gene 91:217–223, 1990), the CAG promoter (Niwa et al., Gene 108:193–200, 1991), the RSV LTR promoter (Cullen, Methods in Enzymol. 152:684–704, 1987) the SRα promoter (Takebe et al., Mol. Cell. Biol. 8:466, 1988), the CMV immediate early promoter (Seed et al., Proc. Natl. Acad. Sci. USA 84:3365–3369, 1987), the SV40 late promoter (Gheysen et al., J. Mol. Appl. Genet. 1:385–394, 1982), the Adenovirus late promoter (Kaufman et al., Mol. Cell. Biol. 9:946, 1989), the HSV TK promoter and so on. The introduction of the gene into animal cells to express a foreign gene can be performed according to any methods, for example, the electroporation method (Chu et al., Nucl. Acids Res. 15:1311–1326, 1987), the calcium phosphate method (Chen et al., Mol. Cell. Biol. 7:2745–2752, 1987), the DEAE dextran method (Lopata et al., Nucl. Acids Res. 12:5707–5717, 1984), Sussman et al., Mol. Cell. Biol. 4:1642–1643, 1985), the Lipofectin method (Derijard, Cell 7:1025–1037, 1994; Lamb et al., Nature Genetics 5:22–30, 1993; Rabindran et al., Science 259:230–234, 1993), and so on. The protein of the present invention can be expressed as a fusion protein comprising a recognition site (epitope) of a monoclonal antibody by introducing the epitope of the monoclonal antibody, whose specificity has been revealed, to the N- or C-terminus of the protein of the present invention. A commercially available epitope-antibody system can be used (Experimental Med. 13:85–90, 1995). Vectors which can express a fusion protein with, for example, β-galactosidase, maltose binding protein, glutathione S-transferase, green florescence protein (GFP) and so on by the use of its multiple cloning sites are commercially available.

A fusion protein prepared by introducing only small epitopes consisting of several to a dozen amino acids so as not to change the property of the protein of the present invention by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage), and such, and monoclonal antibodies recognizing them can be used as the epitope-antibody system for screening proteins binding to the protein of the present invention (Experimental Med. 13:85–90, 1995).

The screening system provided by the present invention can be conducted as an in vitro assay system. A specific example of such in vitro assay system is a cell-free system. Specifically, in the screening that is targeting for the binding of proteins as above, such proteins are used in combination, and any one of them is linked to a support. Then, one or two of the others and a test sample are added thereto and incubated. After the support is washed, the binding of the latter protein to the former linked to the support is detected or measured.

The proteins to be used in the present invention may be purified or crude proteins that are produced by cells inherently expressing the proteins, cells in which DNAs encoding the proteins are introduced, or animals or plants in which DNAs encoding the proteins are introduced.

The proteins to be used in the present invention may be linked to a support. First, any one of TRAF6, TAB2, or TAK1, which is purified or crude, is linked to a support. The immobilization of the protein on a support may be performed by a standard method. Supports for the protein immobilization are, for example, insoluble polysaccharides such as agarose, dextran, and cellulose, synthetic resins such as polystyrene, polyacrylamide, and silicon, etc. More specifically, commercially available beads or plates, which are manufactured from them as raw materials, are used. In the case of beads, a column or the like may be used as packed with the beads. Such a plate can be a multi-well plate (96-well multi-well plate, etc.) or a biosensor chip.

The immobilization of protein on a support can be performed by a commonly used method in which chemical bonding, physical adsorption, or the like is used. Alternatively, protein can be linked to a support where an antibody specifically recognizing the protein is pre-immobilized by binding the antibody to the protein. Protein can also be immobilized via avidin/biotin.

The binding between proteins is generally allowed in a buffer. The buffer is, for example, phosphate buffer, Tris buffer, or the like. Incubation condition may be a commonly used one, for example, a condition where incubation is carried out at 4° C. to room temperature for 1 to 24 hours. Washing condition after the incubation can be any of possible condition as far as the wash does not have any negative effects on the protein binding, and for example, buffers containing detergents are usable. Such detergents include, for example, 0.05% Tween20.

In order to select a target compound, each proteins and a test sample are incubated under an adequate condition, and then washed to separate the specific binding from non-specific one. The state of binding between TRAF6 and TAB2, binding between TAB2 and TAK1, or formation of a complex that comprises TRAF6, TAB2, and TAK1 may be then evaluated, depending on the screening method as above.

In the selection of a target compound, each protein is linked to a support. For example, when TRAF6 is intended to be linked to a support, TRAF6 is first immobilized on a support, and then a pre-mixture of the rest of protein and a test sample may be added thereto, or alternatively the rest of protein may be added thereto after addition of a test sample. Alternatively, when TAB1 is intended to be immobilized on a support, likewise, a pre-mixture of the rest of protein and a test sample may be added, or alternatively the rest of protein may be added after addition of a test sample. When TAK1 is intended to be immobilized on support, it is conducted in the same manner. Each proteins and a test sample added in the order as described above are incubated under an adequate condition, and then the state of TRAF6-TAB2 binding, TAB2-TAK1 binding, or formation of a complex that comprises TRAF6, TAB2, and TAK1 can be evaluated.

Together with a testing group where test samples are contacted with the protein, a control group may be used in the inventive screening method. Such control groups can be either of a negative control group without any test samples or positive control group, or both the groups.

When the bound protein is detected or measured by the inventive method, the bound protein may be just detected or quantitatively measured. In both cases, the target compound can be detected by comparing the results obtained for a negative control group without test samples, a group containing test samples, and/or a positive control group.

The activity of the target compound can be quantitatively measured by comparing values obtained from these results. In the quantitative measurement, the values obtained for the negative control group without test samples are compared with those for the groups with test samples, to detect the target compound. As compared with that for the negative control, the value with a test sample is lower, then the test sample can be judged to contain the target compound.

Further, in the case of quantitative measurement, the sample can be quantified based on a standard curve prepared by using values for a positive control group containing known amounts of a compound that is clarified to be capable of inhibiting the binding between TRAF6 and TAB2, the binding between TAB2 and TAK1, or the formation of a complex that comprises TRAF6, TAB2, and TAK1. When the protein bound is larger in quantity, then it can be estimated that the compound has only lower activity for inhibition of the protein binding. On the other hand, when the amount of protein bound is smaller, the binding-inhibitory activity of the compound to inhibit the binding of the protein is presumed to be stronger.

In the present invention, a biosensor, which is based on surface plasmon resonance phenomenon, can be used to detect or measure the binding protein. By using the biosensor based on surface plasmon resonance phenomenon, the protein-protein interaction can be observed in real time as a surface plasmon resonance signal without labeling even when the amount of protein is a trace level (for example, BIACORE (biosensor), Pharmacia). Accordingly, the binding of the proteins used in the present invention can be estimated by using a biosensor such as BIACORE (biosensor).

Specifically, any one of proteins to be used for screening is immobilized on the sensor chip, the other protein is contacted with the sensor chip, then the latter protein bound to the immobilized one is detected as a differential resonance signal.

Such an experiment can be conducted specifically as follows. Initially, a sensor chip CM5 (Biosensor) is activated, and either of TAK1 or TAB1 is immobilized on the sensor chip. More specifically, an aqueous EDC/NHS solution (200 mM EDC (N-ethyl-N'-(3-dimethylaminopropyl) carbonate hydrochloride) and 50 mM N-hydroxysuccinimide (NHS)) is used for the activation of the sensor chip, and then the sensor chip is washed with HBS buffer (10 mM HEPES pH7.4, 150 mM NaCl, 3.4 mM EDTA, 0.05% Tween20).

Subsequently, an adequate amount of a protein exhibiting the interaction is dissolved in HBS buffer, and the solution is contacted with the sensor chip for the immobilization. After the sensor chip is washed with HBS buffer, the residual active groups on the sensor chip are blocked by ethanolamine solution (1 M ethanolamine hydrochloride, pH8.5). Again, the sensor chip is washed with HBS buffer. The resulting chip is used for the binding evaluation.

In the next step, an adequate amount of the protein dissolved in HBS buffer is injected onto the sensor chip. Then, the amount of protein, which interacts to bind to the protein immobilized on the sensor chip, is observed as an increase in the resonance signal values.

Further, in the above-mentioned binding evaluation system, a test sample is injected after the injection of the protein (or two proteins in the case of a complex comprising three proteins) capable of interacting the other protein. Together with the testing group where test samples are injected, a control group may be used. Such control groups can be either of a negative control group without any test samples or positive control group, or both the groups.

The protein bound can be measured quantitatively as a differential resonance signal value. In this case, the results obtained for the negative control group without test samples are compared with those for the groups with test samples and/or for the positive control group, to detect and identify the target compound.

In the present invention, either of the proteins is labeled, and the label on the protein can be utilized to detect or measure the protein binding.

For example, in the above-mentioned screening method, one protein, which is to be mixed with a test sample and to be contacted with the other protein, is pre-labeled, and then incubated in combination with the test sample. After wash, the bound protein is detected or measured based on the label on the protein. Namely, the labeled protein and the test sample are preferably contacted with the other protein linked to the support. After the incubation, the support is washed, and then the label on the bound protein is detected or measured.

The proteins to be used in the present invention can be labeled according to a common method. Labeling substances include, for example, radioisotope, enzyme, fluorescent substance, biotin/avidin, and the like. These labeling substances may be commercially available ones. Examples of radioisotope are $^{32}P$, $^{33}P$, $^{131}I$, $^{125}I$, $^{3}H$, $^{14}C$, and $^{35}S$. The enzyme includes, for example, alkaline phosphatase, horseradish peroxidase, β-galactosidase, β-glucosidase, and the like. The fluorescent substance is exemplified by fluorescein isothiocyanate (FITC), and rhodamine. All these are commercially available, and the labeling with them can be performed by a known method.

Procedures are specifically as follows. Namely, a solution containing either of the proteins is added to a plate, and the plate is allowed to stand still overnight. After wash of the plate, blocking, for example with BSA, is conducted to avoid non-specific binding of proteins. The plate is washed again, and a test sample and the labeled protein are added thereto. A negative control group without test samples and/or positive control group is contained in this experiment. All to be tested are incubated, and then the plates are washed, and finally the bound protein is detected or measured. In the step of detection or measurement, radioisotope can be detected or measured by using liquid scintillation. When the label is an enzyme, a substrate is added to the system and the detection or measurement is based on an enzymatic change of substrate, for example, coloration, which can be detected or measured in an absorbance spectrometer. Fluorescent substances may be detected or measured in a fluorophotometer. These results are compared with values obtained for the control groups to identify the target compound.

In the present invention, an antibody specifically recognizing any one of the proteins, in the combination of each proteins, can be used to detect or measure the bound protein.

For example, together with a test sample, one protein is contacted and incubated with the other protein, after wash, the bound protein is detected or measured with a primary antibody specifically recognizing the protein. Namely, the protein and the test sample are preferably contacted with the other protein linked to the support. After the incubation, the support is washed, and the bound protein is detected or measured by utilizing the primary antibody specifically recognizing the bound protein. The primary antibody is preferably labeled with a labeling substance.

Such an experiment can be conducted specifically as follows. A solution containing either of the proteins is added to a plate, and the plate is allowed to stand still overnight. After wash of the plate, blocking, for example with BSA, is conducted on the plate to avoid non-specific binding of proteins. The plate is washed again, and a test sample and the other protein are added thereto. A negative control group without test samples and/or positive control group is contained in this experiment.

All to be tested are incubated, and then the plates are washed. The antibody against the protein that has been added together with the test sample is added thereto. After appropriate incubation, the plate is washed, and the protein is detected or measured with the primary antibody specifically recognizing the protein. In the step of detection or measurement, radioisotope can be detected or measured by using liquid scintillation. When the label is an enzyme, a substrate is added to the system, and the detection or measurement is based on an enzymatic change of substrate, for example, coloration, which can be detected or measured in an absorbance spectrometer. Fluorescent substances may be detected or measured in a fluorophotometer. The results obtained are compared with those for the control groups to identify the target compound.

In the present invention, a primary antibody specifically recognizing other peptides that are fused with the protein to be used in the present invention can be used to detect or measure the bound protein.

For example, in the above-mentioned screening method, together with a test sample, either one of the proteins is contacted and incubated with the other protein, after wash, the bound protein is detected or measured with a primary antibody specifically recognizing a peptide fused with the protein. Namely, the protein and the test sample are preferably contacted with the other protein linked to the support. After the incubation, the support is washed, and then the bound protein is detected or measured by the primary antibody specifically recognizing the peptide fused with the bound protein. The primary antibody is preferably labeled with a labeling substance.

Such an experiment can be conducted specifically as follows. Namely, a solution containing either of the proteins is added to a plate, and the plate is allowed to stand still overnight. After wash of the plate, blocking, for example with BSA, is conducted on the plate to avoid non-specific binding of proteins. The plate is washed again, and a test sample and another protein fused with a peptide are added thereto. A negative control group without test samples and/or positive control is contained in this experiment.

All to be tested are incubated, and then the plates are washed. The antibody against the peptide fused with the protein that has been added together with the test sample is added thereto. After suitable incubation, the plate is washed, and the protein is detected or measured with the primary antibody specifically recognizing the peptide fused with the protein. In the step of detection or measurement, radioisotope can be detected or measured by using liquid scintillation. When the label is an enzyme, a substrate is added to the system, and the detection or measurement is based on an enzymatic change of substrate, for example, coloration, which can be detected or measured in an absorbance spectrometer. Fluorescent substances may be detected or measured in a fluorophotometer. The results obtained are compared with those for the control groups to identify the target compound.

In the present invention, a primary antibody specifically recognizing the protein to be used in the present invention and a secondary antibody specifically recognizing the primary antibody can be used to detect or measure the bound protein.

For example, together with a test sample, either one of the proteins is contacted and incubated with the other protein, after wash, the bound protein is detected or measured with a primary antibody specifically recognizing the protein and the secondary antibody specifically recognizing the primary antibody. Namely, the protein and the test sample are preferably contacted with the other protein linked to the support. After the incubation and wash, the bound protein is detected or measured by the primary antibody specifically recognizing the protein and the secondary antibody specifically recognizing the primary antibody. The secondary antibody is preferably labeled with a labeling substance.

Such an experiment can be conducted specifically as follows. Namely, a solution containing either of the proteins is added to a plate, and the plate is allowed to stand still overnight. After wash of the plate, blocking, for example with BSA, is conducted on the plate to avoid non-specific binding of proteins. The plate is washed again, and a test sample and the other protein are added thereto. A negative control group without test samples and/or positive control group is contained in this experiment.

All to be tested are incubated, and then the plates are washed, the primary antibody against the peptide fused with the protein that has been added together with the test sample is added thereto. After appropriate incubation, the plate is washed, and then the secondary antibody specifically recognizing the primary antibody is added thereto. After suitable incubation, the plate is washed, and the protein is detected or measured with the secondary antibody specifically recognizing the primary antibody specifically recognizing the protein. In the step of detection or measurement, radioisotope can be detected or measured by using liquid scintillation. When the label is an enzyme, a substrate is added to the system, and the detection or measurement is based on an enzymatic change of substrate, for example, coloration, which can be detected or measured in an absorbance spectrometer. Fluorescent substances may be detected or measured in a fluorophotometer. The results obtained are compared with those for the control groups to select the target compound.

In the present invention, a primary antibody specifically recognizing other peptides that are fused with the protein and a secondary antibody specifically recognizing the primary antibody can be used to detect or measure the bound protein.

For example, in the above-mentioned screening method, together with a test sample, either one of the proteins is contacted and incubated with the other protein, after wash, the bound protein is detected or measured with a primary antibody specifically recognizing a peptide fused with the protein and a secondary antibody specifically recognizing the primary antibody. Namely, the protein and the test sample are preferably contacted with the other protein linked to the support. After the incubation, the support is washed, and then the bound protein is detected or measured by the primary antibody specifically recognizing the peptide fused with the bound protein and the secondary antibody specifically recognizing the primary antibody. The secondary antibody is preferably labeled with a labeling substance.

Such an experiment can be conducted specifically as follows. Namely, a solution containing either of the proteins is added to a plate, and the plate is allowed to stand still overnight. After wash of the plate, blocking, for example with BSA, is conducted to avoid non-specific binding of proteins. The plate is washed again, and a test sample and the other protein fused with a peptide are added thereto. A negative control group without test samples and/or positive control group is contained in this experiment.

All to be tested are incubated, and then the plates are washed, the primary antibody against the peptide fused with the protein that has been added together with the test sample is added thereto. After appropriate incubation, the plate is washed, then the secondary antibody specifically recognizing the primary antibody is added thereto. After suitable incubation, the plate is washed, and the protein is detected or measured with the secondary antibody specifically recognizing the primary antibody specifically recognizing the peptide fused with the protein. In the step of detection or measurement, radioisotope can be detected or measured by using liquid scintillation. When the label is an enzyme, a substrate is added to the system, and the detection or measurement is based on an enzymatic change of substrate, for example, coloration, which can be detected or measured in an absorbance spectrometer. Fluorescent substances may be detected or measured in a fluorophotometer. The results obtained are compared with those for the control groups to determine the target compound.

It can be conducted particularly preferably by Enzyme-linked Immunosorbent Assay (ELISA) as follows. Specifically, TAK1 fused with a peptide, for example 6×His, is diluted with an immobilization buffer (0.1 M $NaHCO_3$, 0.02% $NaN_3$, pH9.6). Appropriate amounts of the aqueous solution of dilution are added to respective wells of a 96-well immuno-plate (Nunc) and incubated at 4° C. overnight.

Each well is washed 3 times with a washing buffer (prepared as PBS containing 0.05% Tween20), and 200 µl of PBS containing 5% BSA (SIGMA) is added thereto, and then the plate was incubated for blocking at 4° C. overnight.

Subsequently, each well is washed 3 times with the washing buffer, adequate amounts of the other protein fused with a peptide (e.g., FLAG), which has been diluted with a dilution buffer (1% BSA and 0.5% Tween20 in PBS) and a test sample are added thereto. The resulting mixture is incubated at room temperature for 1 hour. Each well is washed 3 times with the washing buffer, and a 100-µl aliquot of mouse anti-FLAG M2 antibody (IBI), which has been diluted to 3 µg/ml with the dilution buffer, is added to each well. The plate is incubated at room temperature for 1 hour.

Each well is washed 3 times with a washing buffer, and a 100-µl aliquot of alkaline phosphatase-labeled goat anti-mouse IgG antibody (ZYMED), which has been diluted 1000 times with the dilution buffer, is added to each well. The plate is incubated at room temperature for 1 hour. Each well is washed 5 times with a washing buffer, and a 100-µl aliquot of a coloring solution (substrate buffer (50 mM $NaHCO_3$, 10 mM $MgCl_2$, pH9.8) containing 1 mg/ml p-phenylphosphate; SIGMA) is added to each well. The plate is incubated at room temperature, and then absorbance at 405 nm is measured by using a microplate reader (Model3550, BIO-RAD). The results obtained are compared with those for the negative control group and/or positive control group to identify the target compound.

In addition, protein G or protein A instead of the secondary antibody can be utilized in the detection or measurement using the antibody of the present invention.

The inventive screening method can be practiced by using High Throughput Screening (HTS). Specifically, the steps from the start to the blocking are performed manually, and the remaining reactions are automated by using a robot, thereby achieving a high-throughput screening.

Specifically, any one of proteins fused with a peptide, for example 6×His, is diluted with an immobilization buffer (0.1 M $NaHCO_3$, 0.02% $NaN_3$, pH9.6). Appropriate amounts of the aqueous solution of dilution are added to respective wells of a 96-well immuno-plate (Nunc) and incubated at 4° C. overnight.

Each well is washed 3 times with a washing buffer (prepared as PBS containing 0.05% Tween20), and 200 µl of PBS containing 5% BSA (SIGMA) is added thereto, and then the plate was incubated for blocking at 4° C. overnight.

Subsequently, for example, the immuno-plate subjected to the blocking treatment is placed in a BIOMEK2000 HTS system (Beckman), and the device is operated by a system control program. In this process, a dispenser such as BIOMEK 2000 dispenser (Beckman) or Multipipette 96-well dispenser (Sagian) can be used to dispense solutions to each well or to remove them from well of the immuno-plate. Further, EL404 microplate washer (Bio Tek) can be used to wash each well of the immuno-plate. Absorbance can be measured by using a SPECTRAMAX250 plate reader (Molecular Devices).

The operating program is set to conduct the following steps. Specifically, each well is washed 3 times with the washing buffer, and then adequate amounts of a test sample and the other protein fused with a peptide, for example maltose-binding protein (MBP), which has been diluted with a dilution buffer (1% BSA and 0.5% Tween20 in PBS), are added thereto. A negative control group without test samples and a positive control are simultaneously managed. These all samples are incubated at room temperature for 1 hour.

Each well is washed 3 times with a washing buffer, and a 100-µl aliquot of rabbit anti-MBP antiserum (New England Biolabs), which has been diluted 5000 times with the dilution buffer, is added thereto. The plate is incubated at room temperature for 1 hour. Each well is washed 3 times with a washing buffer, and a 100-µl aliquot of alkaline phosphatase-labeled goat anti-rabbit IgG antibody (TAGO), which has been diluted 5000 times with the dilution buffer, is added to each well. The plate is incubated at room temperature for 1 hour.

Each well is washed 5 times with a washing buffer, and a 100-µl aliquot of a coloring solution (substrate buffer (50 mM $NaHCO_3$, 10 mM $MgCl_2$, pH9.8) containing 1 mg/ml p-nitrophenylphosphate; SIGMA) is added to each well. The plate is incubated at room temperature, and then absorbance at 405 nm is measured by using a microplate reader, Biomekplate reader (Beckman/Molecular Devices). The results obtained are compared with those for control groups to identify the target compound.

Antibodies to be used in the present invention can be commercially available antibodies and antibodies contained in commercially available kits as well as monoclonal or polyclonal antibodies that can be prepared by using well-known methods. The method for producing antibodies is the same as the method for producing the above-mentioned antibodies against TAB2.

The primary antibody or secondary antibody obtained above can be labeled according to a commonly-known method. Labeling substances include, for example, radioisotope, enzyme, fluorescent substance, and the like. These labeling substances may be commercially available ones. Examples of radioisotope are $^{32}$P, $^{33}$P, $^{131}$I, $^{125}$I, $^{3}$H, $^{14}$C, and $^{35}$S. The enzyme includes, for example, alkaline phosphatase, horseradish peroxidase, β-galactosidase, β-glucosidase, and the like. The fluorescent substance is exemplified by fluorescein isothiocyanate (FITC) and rhodamine. The labeling can be performed by a known method by obtaining these commercially available labeling substances.

The binding between proteins can also be detected and/or measured by observing change in the expression level of a reporter gene which is activated in response to the binding of the proteins. Luciferase, β-galactosidase, HIS3 gene, chloramphenicol acetyltransferase (CAT), green fluorescent protein (GFP) gene, or the like can be used as such reporter gene.

Proteins expressed in cells may be fused proteins with other peptides. The peptides to be fused with the proteins can be any peptides as far as the peptides are usable in the inventive screening method, but are preferably transcriptional regulatory factors.

For example, each of two proteins to be measured its bound are respectively fused with respective subunits of heterodimeric transcriptional regulatory factor that is known to bind to a DNA and thereby activating the transcription of a certain reporter gene to construct DNA. The fusion genes are inserted into expression vectors, and the resulting DNA constructs are introduced into cells (in the case of ternary complex, for example, TAB2 is expressed as it is.). When a test sample does not contain any compound inhibiting the binding between proteins, the two proteins (the three proteins in the case of ternary complex) form the heteromer. The heteromeric transcriptional regulatory factor binds to the DNA and thereby activating the reporter gene.

When a test sample contains a compound inhibiting the binding between proteins, the compound inhibits the binding between proteins. As a result, the subunits of the transcriptional regulatory factor cannot form the heteromer, and thus the transcription of the reporter gene is not induced. The target compound can be detected or measured by observing change in the expression level of a reporter gene. The two-hybrid system (Fields et al., Trends. Genet. 10:286–292, 1994) or three-hybrid system can be used when change in the expression level of a reporter gene is intended to be assayed in such a system.

The hybrid system may be constructed by using a commonly used method or by utilizing a commercially available kit. Examples of the commercially available two-hybrid system kit are MATCHMAKER Two-Hybrid System, Mammalian MATCHMAKER Two-Hybrid Assay Kit (both are products from CLONTECH), and HYBRIZAP Two-Hybrid Vector System (Stratagene).

Specifically, the following procedure is employed for the experiments. The gene encoding either one protein is ligated with the gene encoding LexA DNA-binding domain to provide an expression vector. The desired gene fragments are inserted into yeast two-hybrid expression plasmid pBTM116 (Vojtek et al., Cell 74:205–214, 1993) to construct an expression vector.

Next, the other is ligated with the gene encoding GAL4-transcription activation domain to prepare an expression vector. As the expression vector, for example, yeast two-hybrid expression plasmid pGAD10 (CLONTECH) can be used.

Each of the two-hybrid expression plasmids is transformed into cells of yeast L40 strain containing the HIS3 gene of which transcription is regulated by a promoter with a LexA-binding motif. When the cells are incubated on synthetic medium without histidine, the presence of the protein interaction results in yeast growth. Thus, the degree of transformant growth indicates increases in the expression level of the reporter gene, and the target compound can be screened.

In addition, another embodiment of screening method for compounds that inhibit the signal transduction of IL-1 is that in which inhibition of biological activity transduced through TAB2 protein is used as index. Specifically, the method comprises the following steps of: (a) contacting IL-1 with a mammalian cell that expresses TAB2 protein in the presence of a test sample; (b) detecting the biological activity that is transduced through TAB2 protein; and (c) selecting a compound that decreases the biological activity.

There is no restriction on test samples, for example, cell culture supernatant, products of fermentative microorganisms, marine organism extracts, plant extracts, prokaryotic cell extracts, eukaryotic single cell extracts, animal cell extracts, or library thereof, purified or crude proteins, peptides, non-peptide compounds, synthetic low molecular compounds, or natural compounds can be used.

As to cells used for screening, there is no restriction so long as they are mammalian cells that can transduce signals in response to IL-1 stimuli. For example, 293 cell that has expressed IL-1 receptor can be use suitably. A vector that expresses exogenous TAB2 is inserted into the cell as required. When the cell does not retain proteins involved in signal transduction of IL-1, it is possible to artificially produce signal transduction system by introducing exogenous genes.

The biological activity used as index in the screening method includes, for example, activation of TAK1, activation of NF-κB, activation of JNK, translocation of TAB2 protein from cell membrane to cytoplasm, autophosphorylation of TAK1, and so on.

It was demonstrated that activated TAK1 activates kinase activity of MAPKK by phosphorylating MAPKK, for example, MKK3 (Moriguchi et al., J. Biol. Chem. 271: 13675–13679, 1996), MKK6 (Moriguchi et al., J. Biol. Chem. 271:13675–13679, 1996), or XMEK2/SEKI (Shibuya et al., Science 272:1179–1182, 1996) due to its kinase activity. As substrates of phosphorylation of TAK1, such proteins can be used. For example, it is possible to detect phosphorylation activity of TAK1 by detecting phosphorylation of MMK6. The reaction of phosphorylation activity of TAK1 can occur within cells, or in vitro after extraction of proteins from cells.

An in vitro kinase assay system using, for example, TAK1 is utilized to conduct the screening where TAK1 kinase activity is used as an index. TAK1 reacted with a test sample is separated from cell extracts using anti-TAK1 antibodies or the like. To the separated TAK1, a substrate protein for TAK1, such as MKK6, is added together with $^{32}$P-ATP, thereby performing kinase reaction. The activity is then detected or measured. After the kinase reaction, the amount of $^{32}$P-ATP incorporated into the substrate protein by the phosphorylation thereof is assayed to evaluate the TAK1 kinase activity. The result is compared to that of a negative control without any test sample to identify a compound directly inhibiting TAK1 kinase activity. Such an in vitro kinase assay system for TAK1 is exemplified by the one as described in a reference (Moriguchi et al., J. Biol. Chem. 271:13675–13679, 1996).

The screening method using TAK1 kinase activity as an index can be used for High Throughput Screening (HTS). Specifically, the steps of addition, mixing, and respective reactions for each sample are automated by using a robot, the phosphorylation degree of substrate protein is detected by scintillation proximity assay method (Bothworth et al., Nature 341:167–168, 1989), and thereby achieving a high-throughput screening.

Specifically, TAK1 prepared from cells is added to each well of 96-well microplate. Subsequently, $^{32}$P-ATP and a substrate protein (e.g., MKK6) are added to the above-mentioned reaction solutions for the kinase reaction. In the next step, an anti-MKK6 antibody is added to each well, and then SPA beads (Amersham) which are coated by protein A or an antibody specifically recognizing other antibodies in a species-specific manner are added to each well. After incubation, radioactivity incorporated into the substrate protein is measured by using a MicroBeta scintillation counter (Wallac). Alternatively, when biotinylated substrate protein is used, streptavidin-coated SPA beads can be used for the assay. The result obtained by these methods is compared to that of a control group to identify a test sample containing a compound inhibiting TAK1 kinase activity.

It was shown in Examples that an expression of TAB2 induces activation of NF-κB or JNK. It was demonstrated that dominant negative mutant of TAB2 inhibits activation of NF-κB or JNK. Thus, such biological activities can be used as index for screening method of the present invention.

The activation of NF-κB can be detected, for example, by introducing, into cells, a vector containing a reporter gene linked downstream of Ig-κ promoter, and utilizing the expression of the reporter gene within the cells as index.

Specifically, for example, a reporter gene construct containing the luciferase gene which is regulated by an NF-κB response element derived from the IFN-β gene (p55IgkLuc; Fujita et al., Gene Dev. 7:1354–1363, 1993) is introduced into 293 cells expressed IL-1 receptor in which the expression plasmids corresponding to respective genes are introduced and also into the control cells in which an expression vector without gene insert has been introduced. The respective cells are cultured in medium with or without 10 ng/ml of IL-1. Luciferase activity is then assayed in the cell extracts.

As a result, when cells to which a test sample was added have lower luciferase activity, compared with that of cells without addition of the test sample, it is determined that the compound contained within the test sample inhibits IL-1 signal transduction. Thus, by comparing expression level of reporter genes with control, the desired compound can be screened.

On the other hand, the activation of JNK can be detected, for example, by phosphorylation of Jun as described in Examples. Specifically, for example, an expression vector encoding JNK and an expression vector encoding TAB2 are cotransfected into 293 cell that has expressed IL-1 receptor, and IL-1 affects the cell. The cell extracts are subjected to immunoprecipitation to obtain JNK, and the immunoprecipitation products are subjected to in vitro phosphorylation assay using Jun as substrates. As a result, when cells to which a test sample was added have lower level of phosphorylation on substrates, compared with that of cells without addition of the test sample, it is determined that the compound contained within the test sample inhibits IL-1 signal transduction.

Also, it was shown in Examples that TAB2 protein located on cell membrane is translocated to cytoplasm in response to IL-21 stimuli. Thus, the screening of the present invention can be done using the translocation of TAB2 protein from cell membrane to cytoplasm as index.

The translocation of TAB2 protein from cell membrane to cytoplasm can be detected as described in Examples, for example, by separating membrane fraction and cytoplasm fraction from samples and detecting TAB2 protein contained in such fractions. Alternatively, using antibodies against TAB2, the intracellular localization of TAB2 can be detected in situ by cellular immunochemically method. It is also achieved by labeling fusion proteins comprising TAB2 and other peptides (for example, proper epitope or fluorescent protein such as GFP) and measuring the intracellular distribution of such fusion proteins. As a result, when cells to which a test sample was added have lower translocation level of TAB2 protein into cytoplasm, compared with that of cells without addition of the test sample, it is determined that the compound contained within the test sample inhibits IL-1 signal transduction.

The present invention also provides inhibitory agents of IL-1 signal transduction, where the inhibitory agents include, as active ingredient, compounds isolatable by screening method of the present invention. Herein the term "inhibitory agent of IL-1 signal transduction" encompasses reagents and medicaments for inhibiting signal transduction of IL-1. Reagents for inhibiting IL-1 signal transduction can be inhibitory agents of molecules involved in signal transduction in response to IL-1 stimuli, such as JNK and NF-κB. Also, since it is believed that IL-1 is involved in progress of various diseases such as inflammation and allergic diseases, for example, septicemia, rheumatoid arthritis, asthma, nephritis, hepatitis, and pneumonia, the compound that inhibits signal transduction of IL-1 mediated by TAB2 is expected to be used as medicament for treatment or prevention of such diseases.

In one embodiment, inhibitory agents of IL-1 signal transduction of the present invention include, as active ingredient, compounds that inhibit the binding between TAB2 protein or peptide and TAK1 protein and/or TRAF6 protein. Another embodiment of the inventive inhibitory agents for IL-1 signal transduction is mutant or partial peptide of TAB2. An example of such is dominant negative mutant of TAB2 that has an amino acid sequence comprising amino acids at 401 through 693 of the amino acid sequence set forth in SEQ ID NO:2. Although this dominant negative mutant has binding activity with TRAF6 and TAK1, it cannot form the complex comprising the three, and thus it does not activate kinase activity of TAK1. Therefore, the dominant negative mutant of TAB2 does not transduce signals downstream of TAK1 and inhibits the binding between normal TAB2 and TRAF6 or TAK1.

When administrating such compound that has activity for inhibiting signal transduction of IL-1 as a pharmaceutical for humans and other mammals, such as humans, mice, rats, guinea-pigs, rabbits, chicken, cats, dogs, sheep, pigs, cattle, monkeys, baboons, chimpanzees, the protein or isolated compound can be directly administered or can be formulated into a dosage form using known pharmaceutical preparation methods.

For example, according to the need, the drugs can be taken orally, as sugar-coated tablets, capsules, elixirs and microcapsules, or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 (TM) and HCO-50.

Sesame oil or Soy-bean oil can be used as a oleaginous liquid and may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an antioxidant. The prepared injection may be filled into a suitable ampule.

Methods well known to one skilled in the art may be used to administer the inventive pharmaceutical compound to patients, for example as intraarterial, intravenous, percutaneous injections and also as intranasal, transbronchial, intramuscular, transdermal, or oral administrations. The dosage and method of administration vary according to the body-weight and age of a patient and the administration method; however, one skilled in the art can routinely select them. If said compound is encodable by a DNA, the DNA can be inserted into a vector for gene therapy and the vector administered to perform the therapy. The dosage and method of administration vary according to the body-weight, age, and symptoms of a patient but one skilled in the art can select them suitably.

Although a dosage of the protein of the invention changes according to the subject to be treated, the target organs, symptoms, and administration methods, it is generally considered to be, for example, about 100 μg to 20 mg one day for an adult (as body-weight 60 kg) in the form of injections.

Although there are some differences according to the symptoms, it is believed that the dose of a compound that inhibits signal transduction through TAB2 of the present invention is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it may be convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight or to body surface area.

Figure 1B:
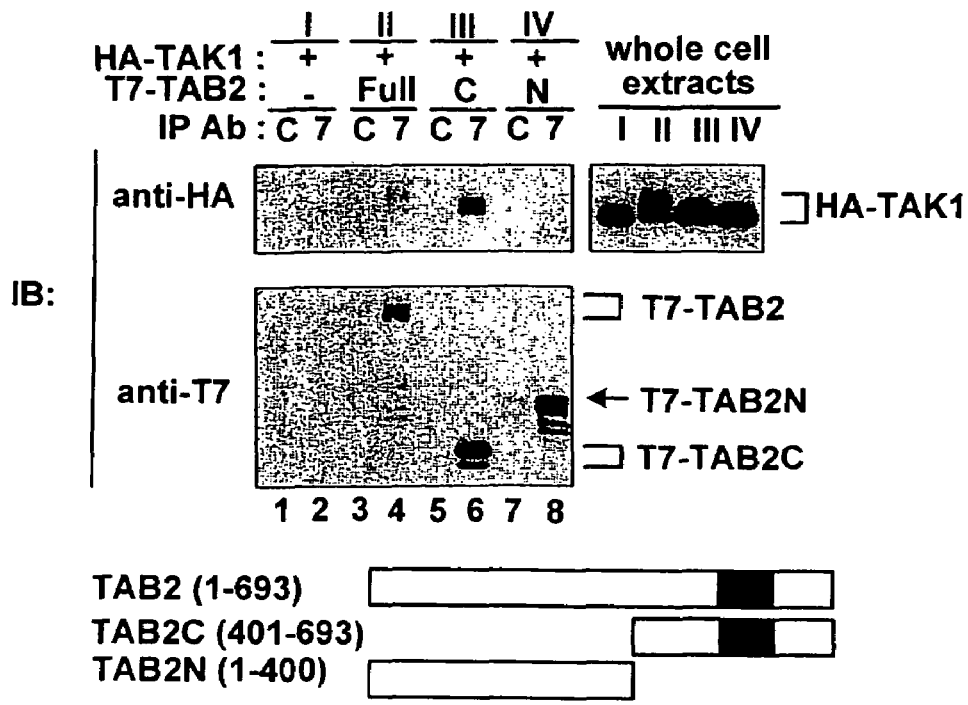
FIG. 1 shows isolation of TAB2.

(A) shows an amino acid sequence of TAB2 (SEQ ID NO2). The sequences obtained from yeast two-hybrid screening with TAK1 are boxed. The coiled-coil region is underlined.

(B) shows an association of TAB2 with TAK1 in mammalian cells. 293 cells were transiently transfected with an expression vector for HA-TAK1 in combination with empty vector (−) or with expression vectors for T7-TAB2-Full length (Full), T7-TAB2C (C), or T7-TAB2N (N) as indicated. Cell extracts were immunoprecipitated (IP) with anti-T7 (7) or mouse IgG (C). Coprecipitated HA-TAK1 was detected by immunoblotting (IB) with anti-HA (upper panel, left). The amounts of immunoprecipitated T7-TAB2 proteins were determined with anti-T7 (lower panel). Whole cell extracts were immunoblotted with anti-HA to determine total amounts of HA-TAK1 (upper panel, right). Schematic representation of various TAB2 constructs is shown in the lower part. The coiled-coil regions are indicated by solid boxes.

(C) shows effects of TAB1 and TAB2 on TAK1 in yeast cells. Yeast strain SY1984 was transformed with an expression vector encoding TAK1-HA and expression vectors encoding either TAB1 or TAB2 as indicated. TAK1-HA was immunoprecipitated (IP) from each cell extract, and immunoprecipitates were subjected to in vitro phosphorylation assays using bacterially expressed MKK8 as an exogenous substrate (top panel). No extract (N/E) indicates the phosphorylation assay performed without yeast extracts, corresponding to the autophosphorylation of MKK6. The amounts of TAK1, TAB1 and TAB2 in each immune complex were determined by immunoblotting (IB) with anti-HA (middle panel), anti-TAB1 and anti-TAB2 (bottom panel), respectively.

FIG. 2 shows effects of TAB2 on IL-1- and TGF-β-mediated pathways.

(A) shows effects of TAB2 on NF-κB activation. 293 cells were transiently transfected with the reporter vector Ig-κ-Luciferase and pAct-β-Gal in combination with empty vector (−) or with the indicated amounts of expression vectors for the full-length of TAB2 [Full (1–693)], TAB2C [C (401–693)], or TAB2N [N (1–400)]. Cells were either left untreated, or treated with IL-1 (10 ng/ml) for 24 hours (+IL-1). Luciferase activities were determined and normalized to levels of β-galactosidase activity. The fold increase in luciferase activity relative to cells transfected with empty vector is shown.

(B) shows effects of TAB2 on JNK activation. 293 cells were transiently cotransfected with an expression vector encoding HA-JNK and expression vectors encoding either TAB2 or TAB2C as indicated. 24 hours after transfection, cells were either left untreated, or treated with IL-1 (10 ng/ml) for 30 min (+). HA-JNK was immunoprecipitated from each cell extract, and immunoprecipitates were subjected to in vitro phosphorylation assays using bacterially expressed GST-cJun as an exogenous substrate (upper panel). The amounts of HA-JNK in each immune complex were determined by immunoblotting with anti-HA (lower panel).

(C) shows effects of TAB2 on 3TP activation. 293 cells were transiently transfected with the reporter vector 3TP-Luciferase and pAct-β-Gal in combination with expression vectors for a constitutively active TGF-β type I receptor [+TβRI (T204D)] and the indicated amounts of expression vectors for the full-length of TAB2 [Full (1–693)], TAB2C

[C (401–693)], or TAB2N [N (1–400)]. Smad7 was used as a positive control that inhibits 3TP activation induced by TβRI (T204D). Luciferase activities were determined and normalized to levels of β-galactosidase activity. The fold increase in luciferase activity relative to cells transfected with empty vector is shown.

FIG. 3 show the interaction of TAB2 with TRAF6.

(A) show an association of TAB2 with TRAF8 in mammalian cells. 293 cells were transiently transfected with an expression vector for 2Flag-TRAF6 in combination with empty vector (−) or with expression vectors for T7-TAB2-Full length (Full) (Full), T7-TAB2C (C), or T7-TAB2N (N) as indicated. Cell extracts were immunoprecipitated (IP) with anti-T7 (7) or mouse IgG (C). Coprecipitated Flag-TRAF6 was detected by immunoblotting (IB) with anti-Flag (upper panel, left). The amounts of immunoprecipitated T7-TAB2 proteins were determined with anti-T7 (lower panel). Whole cell extracts were immunoblotted with anti-Flag to determine total amounts of Flag-TRAF6 (upper panel, right).

(B) shows an association of endogenous TRAF6 with TAB2, TAK1 and TAB1. 293IL-1 R1 cells were left untreated (0 min) or treated with IL-1 (10 ng/ml) for the indicated times. Cell extracts were immunoprecipitated (IP) with anti-TRAF6. Coprecipitated TAB2, TAK1 and TAB1 were detected by immunoblotting (IB) with anti-TAB2 (top panel, left), anti-TAK1 and anti-TAB1 (middle panel, left), respectively. The amounts of immunoprecipitated TRAF6 were determined by immunoblotting with anti-TRAF6 (bottom panel). Whole cell extracts were immunoblotted with anti-TAB2 (top panel, right), anti-TAK1 and anti-TAB1 (middle panel, right) to determine total amounts of TAB2, TAK1 and TAB1, respectively.

FIG. 4 shows IL-1-induced translocation of TAB2.

(A) shows subcellular fractionation of 293IL-1RI cells in the presence or absence of IL-1 stimulation. 293IL-1RI cells were left untreated (0 min) or treated with IL-1 for the indicated times. Cells were fractionated into the membrane (P100) and the cytosolic (S100) fractions, and immunoblotted (IB) with anti-TAB2 (top panel), anti-TAK1 and anti-TAB1 (second panel), anti-TRAF6C (third panel). Asterisks (*) indicate the nonspecific bands detected by anti-TRAF6C. Each fraction was also immunoblotted with anti-β-catenin (fourth panel) and anti-α-tubulin (bottom panel) as a control for the membrane and cytosolic fractions, respectively.

(B) shows an association of TAB2 with TAK1, TAB1 and TRAF6 in the cytosol. 293IL-1RI cells were left untreated (−) or treated with IL-1 (+) (10 ng/ml) for 15 min. S100 fractions from these cells were immunoprecipitated (IP) with anti-TAB2 or rabbit IgG (control IgG). The amounts of immunoprecipitated TAB2 were determined by immunoblotting (IB) with anti-TAB2 (top panel, left). Coprecipitated TAK1, TAB1 and TRAF6 were detected by immunoblotting with anti-TAK1 and anti-TAB1 (middle panel, left), and anti-TRAF6C (bottom panel, left). The total amounts of TAB2, TAK1, TAB1 and TRAF6 in the S100 fraction (S100 Total) were determined by immunoblotting with anti-TAB2 (top panel, right), anti-TAK1 and anti-TAB1 (middle panel, right), and anti-TRAF6C (bottom panel, right). Asterisks (*) indicate the nonspecific bands detected by anti-TRAF6C.

Figure 5:
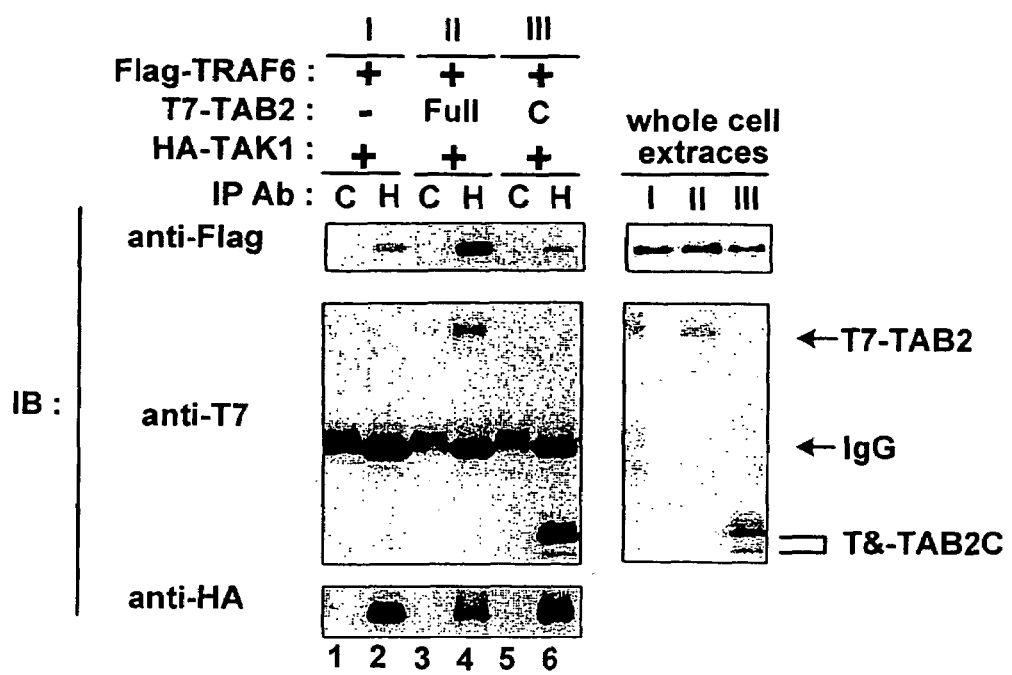

FIG. 5 shows an effect of TAB2 on the interaction between TRAF6 and TAK1.

293 cells were transfected with expression vectors for Flag-TRAF6 and HA-TAK1 in combination with empty vector (−) or with expression vectors for T7-TAB2-Full-length (Full) or T7-TAB2C (C) as indicated. Cell extracts were immunoprecipitated (IP) with anti-HA (H) or mouse IgG (C). Coprecipitated Flag-TRAF6, T7-TAB2 and T7-TAB2C were detected by immunoblotting (IB) with anti-Flag (top panel, left) and anti-T7 (middle panel, left), respectively. The amounts of HA-TAK1 in each immune complex were determined with anti-HA (bottom panel). Whole cell extracts were immunoblotted with anti-Flag and anti-T7 to determine total amounts of Flag-TRAF6, T7-TAB2, and T7-TAB2C, respectively (right panels).

FIG. 6 shows IL-1-induced activation of TAK1 by autophosphorylation.

(A) shows IL-1-induced phosphorylation and activation of TAK1. 293IL-1RI cells were treated with IL-1 (10 ng/ml) for 10 min (+) or left untreated (−). Cell extracts were immunoprecipitated with anti-TAK1 antibody. The immunoprecipitates were left untreated (lanes 1 and 2), or incubated with lambda protein phosphatase (lanes 3 and 4; PPase treatment). All samples were subjected to immunoblotting (IB) with anti-TAK1 and anti-TAB1 antibodies (upper panel), and to an in vitro phosphorylation assay using bacterially expressed MKK6 as an exogenous substrate (lower panel).

(B) shows autophosphorylation of TAK1 induced by IL-1. 293IL-1RI cells were transiently transfected with expression vectors for HA-TAK1, HA-TAK1(K83W), or HA-TAK1 (S192A) as indicated. Cells were treated with IL-1 (10 ng/ml) for 10 min (+) or left untreated (−). The HA-epitope tagged wild type and mutant forms of TAK1 were detected by immunoblotting (IB) with anti-HA.

(C) shows an alignment of the amino acid sequences of the activation loop of TAK1 and other MAPKKKs (SEQ ID NOs:10–18, top to bottom). Asterisks (*) denote residues shown to be phosphorylated and implicated in the activation of these kinases.

(D) shows kinase activities of wild type and the mutant forms of TAK1. 293 cells were transfected with expression vectors for HA-TAK1 (WT), HA-TAK1 (S192A) (SA), HA-TAK1 (S192D) (SD), and TAB1 as indicated. Immunoprecipitates with anti-HA were subjected to in vitro phosphorylation assay using bacterially expressed MKK6 as an exogenous substrate (top panel). The amounts of HA-tagged wild type and mutant forms of TAK1 in each immune complex were determined by immunoblotting (IB) with anti-TAK1 (lower panel).

Figure 7:
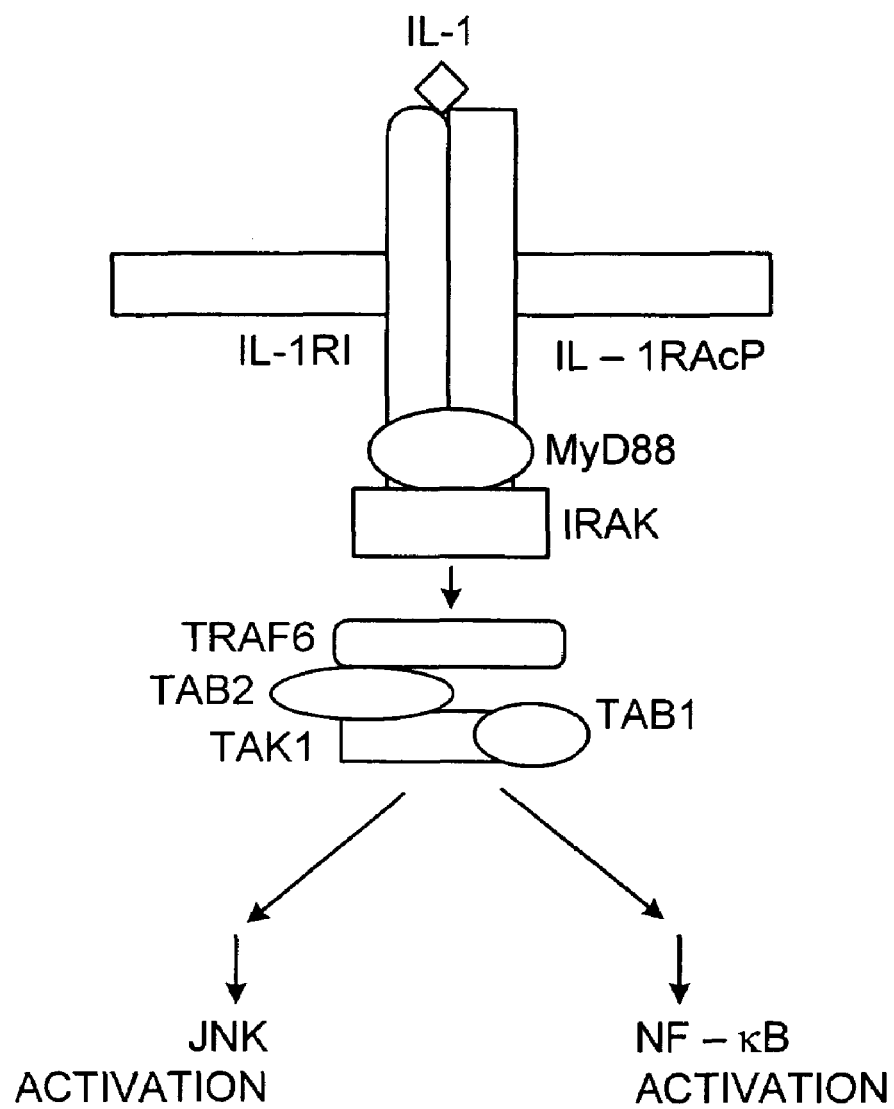

FIG. 7 shows a model of how TAB2 may participate in IL-1 signaling.

The major signaling pathway leading to JNK and NF-κB from IL-1 receptor are indicated. See text for details.

All publications and patents cited herein are incorporated by reference in their entirety.

DETAILED DESCRIPTION

The present invention is illustrated in details by following Examples and references, but is not restricted to them.

EXAMPLE 1

Isolation of TAB2

We screened to identify adaptor proteins acting to allow specificity of response for TAK1 as TAK1-binding proteins using a yeast two-hybrid screening. The present inventors have previously isolated two TAK1-binding proteins, TAB1 and TAB2 (Shibuya et al., Science 272:1179–1182, 1996). TAB1 was found to function as a direct activator of TAK1 (Shibuya et al., Science 272:1179–1182, 1996).

On the other hand, the plasmid pGAD-TAB2 (394–693) encoding TAB2 fragment encodes amino acids 394–693 of TAB2 [TAB2 (394–693)]. A human kidney cDNA library (Clontech) was screened with the TAB2 (394–693) probe, and a 3.3 lb clone was isolated which lacks the N-terminus of TAB2. The 5' end of TAB2 cDNA was isolated by 5' rapid amplification of cDNA ends (5'-RACE) with 5'-RACE-Ready cDNA (Clontech). The full-length cDNA for TAB2 was reconstituted by ligation of a 270-base pair EcoRI-NcoI fragment obtained from the 5'-RACE product and a 2.2 kb NcoI-HindIII fragment of the 3.3 kb clone from the human kidney cDNA library.

Northern (RNA) blot analysis revealed the existence of a single TAB2 transcript expressed in a variety of tissues the size of which, about 5 kb, was consistent with that of the cDNA (data not shown). Sequencing analysis predicted that the TAB2 protein consists of 693 amino acids with a molecular size of 77 kDa (FIG. 1A). One distinctive feature of the TAB2 sequence is the presence of amino acids (535–609) that have the potential to form an amphipathic α-helix. Otherwise, no obvious and significant similarity between TAB2 and any other known protein was found, indicating that TAB2 represents a novel class of proteins.

EXAMPLE 2

Interaction Between TAK1 and TAB2

Cell Culture and Expression Vector 293 and 293IL-1 RI cells used in the following experiments were maintained in Dulbecco's Modified Eagle's medium supplemented with fatal calf serum (10%) at 37° C. and 5% $CO_2$. Mammalian expression vectors encoding TRAF6, TAB1, TAK1, and after-mentioned TAK1 (K63W), have been described previously (Yamaguchi et al., Science 270:2008–2011, 1995; Cao et al., Nature 383:443–446, 1996; Shirakabe et al., J. Biol. Chem. 272:8141–8144, 1997; Ninomiya-Tsuji et al., Nature 398:252–256, 1999). pCMVT7 vector was constructed by inserting a DNA fragment encoding T7 epitope sequence (MASMTGGQQMG; SEQ ID NO:19) into ClaI-EcoRI gap of pCMV, to express the N-terminal T7 epitope tagged proteins under the control of the CMV promoter. pCMVT7-TAB2 was generated by subcloning the open reading frame of TAB2 into pCMVT7 using standard approaches. The truncation mutants, TAB2N and TAB2C, which encode amino acids 1 to 400 and 401 to 693 of TAB2, respectively, were generated as follows. To generate TAB2N mutant, a 250 base-pair fragment was amplified by PCR with a 5'-oligonucleotide (5'-TATAACAT-TCAGAATATTTCAACAGGACCT-3'/SEQ ID NO:3) including an SspI restriction site, and a 3'-oligonucleotide (5'-CAGGTCGACTCACTGTTCATCTCCTGTGGC-3'/ SEQ ID NO:4) incorporating a stop codon and a SalI restriction site. The resulting 250 base-pair SspI-SalI fragment and a 950 base-pair EcoRI-SspI fragment obtained from pCMVT7-TAB2 were inserted into EcoRI-SalI gap of pCMVT7. To generate TAB2C mutant, a 330 base-pair fragment was amplified by PCR with a 5'-oligonucleotide (5'-CGCGAATTCATGCGGAATCAGCCCACACTC-3'/ SEQ ID NO:5) incorporating an EcoRI restriction site, and a 3'-oligonucleotide (5'-CCCCTGGTGAAACTG-CAGGGGGCTTATTGG-3'/SEQ ID NO:6) including a PstI restriction site. The resulting 330 base-pair EcoRI-PstI fragment and a 1 kb PstI-SalI fragment obtained from pCMVT7-TAB2 were inserted into EcoRI-SalI gap of pCMVT7. All constructs were verified by DNA sequencing.

Antibodies and Immunoprecipitation

Antibodies and immunoprecipitation used in Examples are described herein. Polyclonal rabbit antibody to TAB2 (anti-TAB2) was produced against peptides corresponding to amino acids 1 to 20 of TAB2. Polyclonal rabbit antibody to TRAF6 (anti-TRAF6C) was produced against peptides corresponding to amino acids 497 to 522 of TRAF6. Polyclonal goat antibody to TRAF6, TRAF6 (C20) (Santa Cruz), was used for immunoprecipitation of endogenous TRAF6. Polyclonal antibody to TAK1 (anti-TAK1) and polyclonal antiserum to TRAF6 (anti-TRAF6) have been described previously (Lomega et al., Genes Dev. 13:1015–1024, 1999; Ninomiya-Tsuji et al., Nature 398:252–256, 1999). Monoclonal antibodies to HA, HA.11 (Babco), to T7 (Novagen), and to Flag, M2 (Kodak) were used. Purified rabbit and mouse IgG (Sigma) were used as control antibodies.

293IL-1 RI cells were either left untreated or treated with IL-1 (10 ng/ml) for the indicated times. For the transfection studies, 293 cells ($1\times10^6$) were plated in 10 cm dishes, and transfected with a total of 10 μg DNA containing various expression vectors by the calcium phosphate precipitate method, and incubated for 24 to 36 hours. Cells were washed once with ice-cold phosphate-buffered saline (PBS) and lysed in 0.3 ml of 0.5% Triton X-100 lysis buffer containing 20 mM HEPES (pH 7.4), 150 mM NaCl, 12.5 mM β-glycerophosphate, 1.5 mM $MgCl_2$, 2 mM EGTA, 10 mM NaF, 2 mM DTT, 1 mM sodium orthovanadate, 1 mM PMSF, and 20 μM aprotinin. Cellular debris was removed by centrifugation at 10,000 g for 5 min. Proteins from cell lysates were 1 μg of various antibodies and 20 μl of protein G-Sepharose (Pharmacia). The immune complex was washed three times with washing buffer containing 20 mM HEPES (pH 7.4), 500 mM NaCl, and 10 mM $MgCl_2$, and suspended in 40 μl of rinse buffer containing 20 mM HEPES (pH 7.4), 500 mM NaCl, and 10 mM $MgCl_2$. For immunoblotting, the immunoprecipitates or whole cell lysates were resolved on SDS-polyacrylamide gel electrophoresis (SDS-PAGE), and transferred to Hybond-P membranes (Amersham). The membranes were immunoblotted with various antibodies, and the bound antibodies were visualized with horseradish peroxidase-conjugated antibodies to rabbit or mouse IgG using the Enhanced Chemiluminesence (ECL) Western Blotting System (Amersham).

Result

The interaction of TAB2 with TAK1 was investigated using in vivo coprecipitation experiments in mammalian cells. 293 cells were cotransfected with plasmids that express a T7-tagged TAB2 construct and an HA-tagged TAK1 protein, respectively. Cell extracts were immunoprecipitated with a monoclonal antibody to T7, and coprecipitated HA-TAK1 was detected by immunoblotting with a monoclonal antibody to HA (FIG. 1B). TAK1 was found to associate with TAB2 (lane 4). The present inventors also confirmed the physiological relevance of the interaction of TAB2 with TAK1 by showing that endogenous TAB2 and TAK1 associate (see below).

To determine the structural requirements for interaction of TAB2 with TAK1, the present inventors generated two truncated proteins, T7-TAB2N and T7-TAB2C, which contain the N-terminus (amino acids 1 to 400) and C-terminus (amino acids 401 to the end) of TAB2, respectively (FIG. 1B). When coexpressed with HA-TAK1 in 293 cells, TAK1 was found to coprecipitate with TAB2C but not TAB2N (lanes 6, 8). This result indicated that the C-terminal domain of TAB2, which contains the coiled-coil structure, is responsible for its association with TAK1. Conversely, previous work showed that the C-terminal domain of TAK1, which also contains coiled-coil α helices, is responsible for its interaction with TAB2 (Shibuya et al., Science 272:1179–1182, 1996). Thus, these coiled-coil motifs may function as protein-protein interaction domains mediating the contact between TAK1 and TAB2.

EXAMPLE 3

TAB2 does not Act as a Direct Activator of TAK1

Expression Vector and Yeast Culture

Yeast strain SY1984 was cotransformed with pNV11-TAK1-HA and in combination with YEpGAP112 vector, YEpGAP112-TAB1, or YEpGAP112-TAB2. The plasmid YEpGAP112-TAB2 was generated by subcloning the open reading frame of TAB2 into YEpGAP112 vector. The expression plasmids pNV11-TAK1-HA and YEpGAP112-TAB1 were described previously (Shibuya et al., Science 272:1179–1182, 1996). All constructs were verified by DNA sequencing. Transformants (100 ml culture) were grown to an optical density at 600 nm of 0.6. Cell extracts were prepared with a lysis buffer containing 50 mM Tris-HCl (pH 7.5), 100 mM NaCl, 1 mM $Na_4P_2O_7$, 5 mM NaF, 1 mM EDTA, 1% Triton-X 100, 50 mM DOC, 1 mM PMSF, 0.5% aprotinin, and 1 mM DTT, and microcentrifuged at 10,000 g for 5 min. After re-centrifugation at 10,000 g for 10 min, the supernatant was subjected to immunoprecipitation with monoclonal antibodies to HA (HA.11), and assayed for kinase activity as described below.

In vitro Phosphorylation Assay and Phosphatase Treatment

TAK1 or various ectopically expressed HA-epitope tagged proteins were immunoprecipitated with anti-TAK1 or anti-HA, respectively, as described above. Immunoprecipitates were suspended in 40 μl of A-mix buffer containing 20 mM Tris-HCl, and 10 mM $MgCl_2$, and were incubated with 1 μg of bacterially expressed MKK6 (Moriguchi et al., J. Biol. Chem. 271:13675–13679, 1996) in 10 μl of kinase buffer containing 10 mM HEPES (pH 7.4), 1 mM DTT, 5 mM $MgCl_2$, and 5 μCi of [$\gamma$-$^{32}$P]-ATP (3,000 Ci/mmol) at 25° C. for 2 min. Samples were separated by 12% SDS-PAGE and visualized by autoradiography. For phosphatase treatment, immunoprecipitates were incubated with lambda protein phosphatase (New England Biolabs) in the phosphatase buffer containing 50 mM Tris-HCl (pH 7.5), 0.1 mM EDTA, 5 mM DTT, 0.01% Brij 35, and 2 mM $MgCl_2$ at 30° C. for 30 min. Samples were then washed twice with the lysis buffer described above. All samples were subjected to an in vitro phosphorylation assay as described above.

Result

Figure 1C:
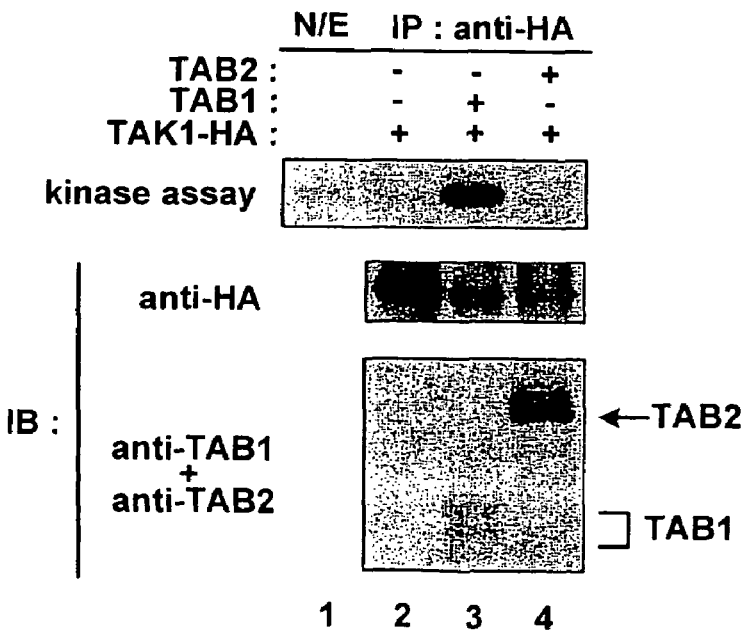

Because TAK1 activity is regulated by TAB1 that binds specifically to TAK1, the present inventors sought to determine if the interaction of TAB2 with TAK1 can regulate its enzymatic activity using yeast cells. Yeast cells were cotransfected with expression plasmids for TAK1-HA and either TAB1 or TAB2. The TAK1 protein was then immunoprecipitated (IP) from transfected yeast cells, and its kinase activity was measured in vitro using a specific substrate MKK6 (FIG. 1C). When the empty vector plasmid was cotransfected, immunoprecipitated TAK1 had little catalytic activity (lane 2). When yeast cells were cotransfected with expression plasmid for TAB1, significant increase of the TAK1 kinase activity was observed (lane 3). This finding is consistent with previously published results indicating that TAB1 functions as an activator of TAK1 (Shibuya et al., Science 272:1179–1182, 1996). On the other hand, coexpression of TAB2 failed to activate TAK1 (lane 4). Therefore, in contrast to TAB1, TAB2 is not a regulator of TAK1 enzymatic activity.

EXAMPLE 4

TAB2 Functions as an IL-1 Signaling Molecule

To determine whether TAB2 participates in IL-1 signal transduction, the present inventors examined its ability to affect NF-κB activation following IL-1 stimulation. The inventors transfected 293 cells with a mammalian vector expressing TAB2 and assayed NF-κB activity using an NF-κB-dependent luciferase reporter.

For the reporter gene assays, 293 cells (1.6×10$^5$ cells/well) were seeded into 6-well (35 mm) plates. At 24 hours after seeding, cells were transfected with a reporter gene plasmid and each expression plasmid as indicated. An Ig-κ-luciferase reporter was used to measure NF-κB-dependent transcription. A plasmid containing β-galactosidase gene under the control of β-actin promoter (pAct-β-Gal) was used for normalizing transfection efficiency. Reporter gene assays were performed as described (Ninomiya-Tsuji et al., Nature 398:252–266, 1999).

Figure 2A:
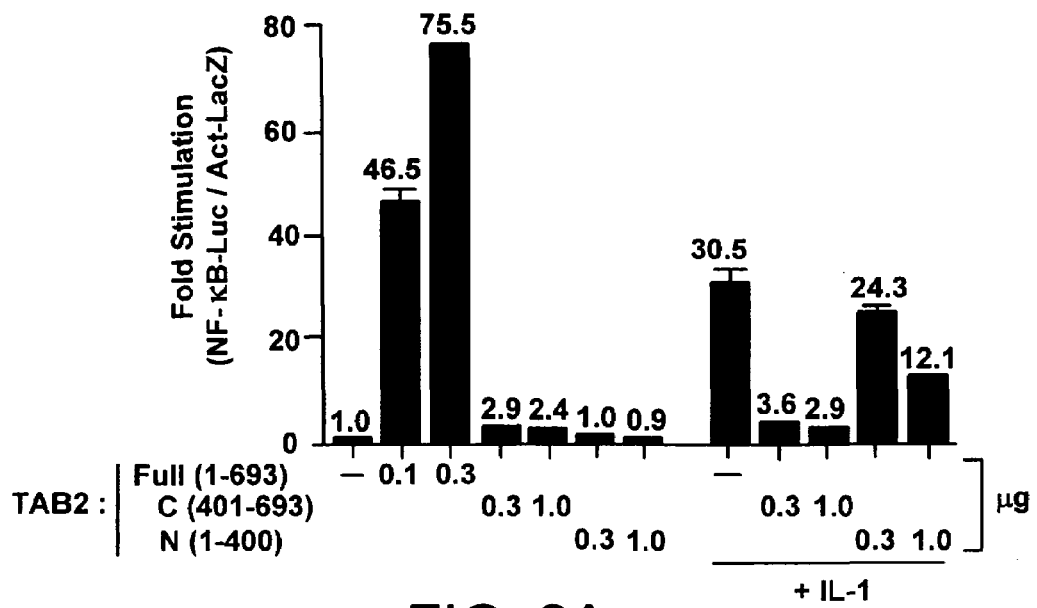
Figure 2C:
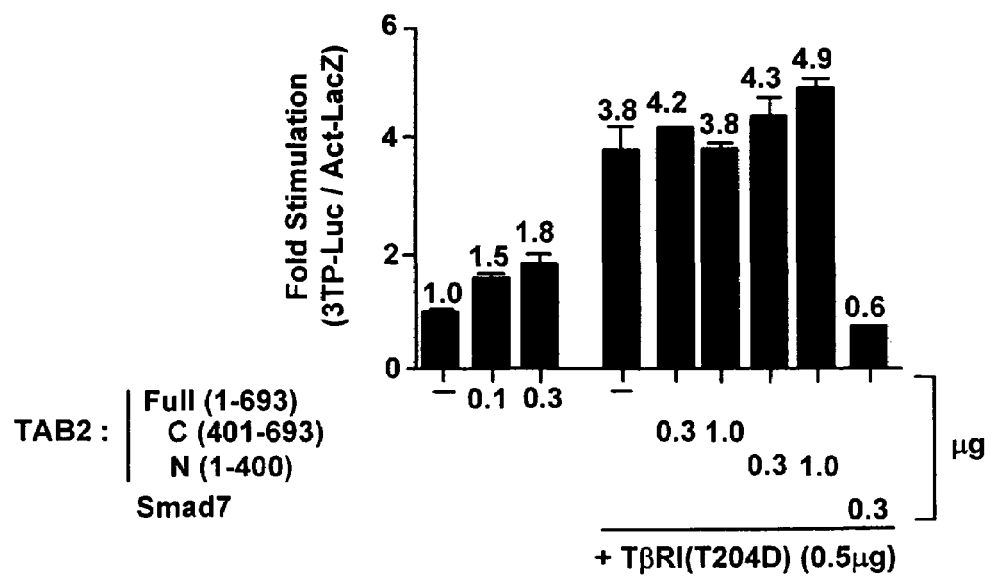
Figure 2B:
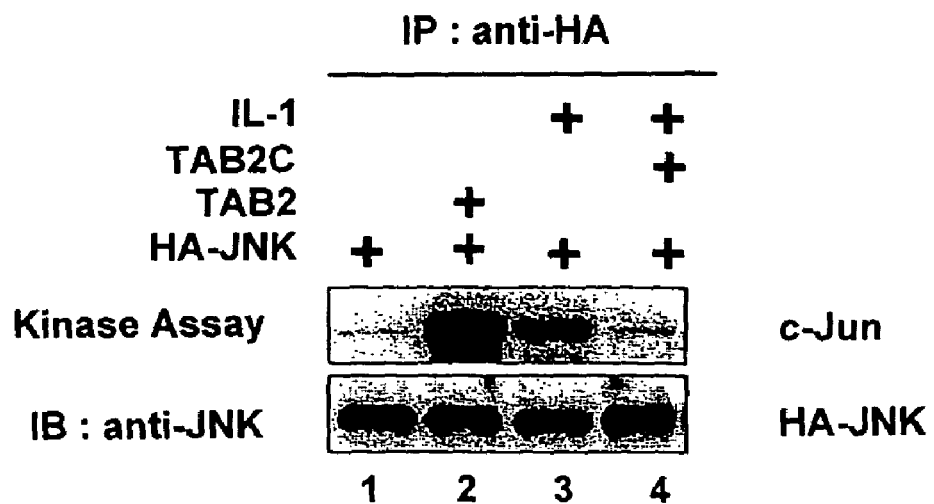

As shown in FIG. 2A, TAB2 activated NF-κB in a dose-dependent manner. Two truncated versions of TAB2, TAB2N and TAB2C (see FIG. 1B), failed to induce any luciferase activity, suggesting that the integrity of TAB2 is essential for its ability to activate NF-κB. Comparable levels of expression of the wild-type and mutant proteins were observed as shown in the Western blot (data not shown). To further elucidate the role of TAB2 in IL-1-mediated NF-κB activation, the present inventors asked whether these truncated variants of TAB2 could act as dominant-negative inhibitors of IL-1-induced NF-κB activity. TAB2C strongly inhibited NF-κB activation by IL-1, whereas TAB2N weakly blocked it (FIG. 2A). These results indicate that TAB2 is required for the activation of NF-κB by IL-1.

In addition to NF-κB activation, IL-1 induces activation of JNK (Dinarello et al., Blood, 87, 2095–2147, 1996). To test whether TAB2 is the molecule responsible for IL-1-mediated activation of JNK, the present inventors analyzed the effect of ectopically expressed TAB2 on JNK activity (FIG. 2B). 293 cells were cotransfected with HA-tagged JNK and either wild-type TAB2 or TAB2C. The extent of JNK activities was determined by immunoprecipitation of JNK followed by an in vitro kinase assay using GST-c-Jun protein as a substrate. Wild-type TAB2 significantly induced activation of JNK (lanes 1, 2). Overexpression of TAB2C inhibited IL-1-induced JNK activation (lanes 3, 4), indicating that TAB2C exerts a dominant-negative effect on IL-1-mediated JNK. Taken together, these results suggest that TAB2 participates in both NF-κB and JNK activation by IL-1.

We next tested the ability of TAB2 to affect TGF-β-mediated signaling using the 3TP-Lux reporter (FIG. 2C), which contains a luciferase gene controlled by TGF-β-responsive element derived from the plasminogen activator inhibitor 1 gene.

Instead of Ig-κ-luciferase reporter as above described, using 3TP-luciferase reporter, TGF-β dependent transcription was measured in the same manner as assay for NF-κB activity. Using plasmids (pAct-β-Gal) containing β-galactosidase gene under regulation of β-actin promoter, transfection efficiency was standardized.

In 293 cells, transfection of TAB2 had little effect on the basal transcription from 3TP-Lux. TGF-β signaling can be initiated by expression of a constitutively active version of the TGF-β type I receptor, [TβRI (T204D)], which signals TGF-β responses in the absence of ligand and the type II receptor. Transfection of TβRI (T204D) increased basal expression of the 3TP-Lux reporter that was potently inhibited by coexpression of a negative regulator Smad7. On the other hand, neither TAB2C nor TAB2N had any effects on 3TP-Lux activity activated by the TβRI (T204D). These results indicate that TAB2 is not involved in TGF-β signaling pathway.

EXAMPLE 5

TAB2 Associates with TRAF6

Figure 3A:
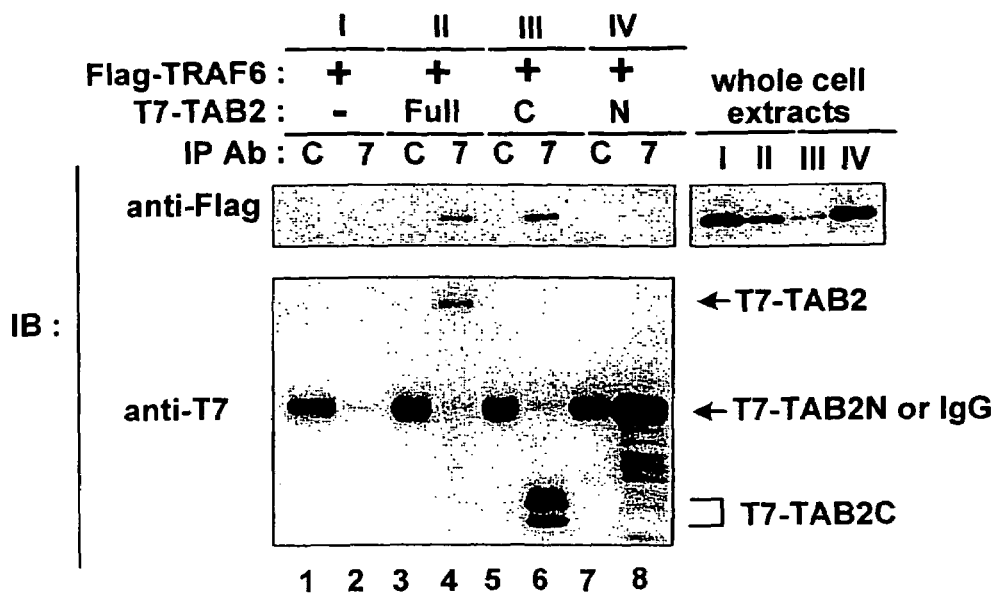
Figure 3B:
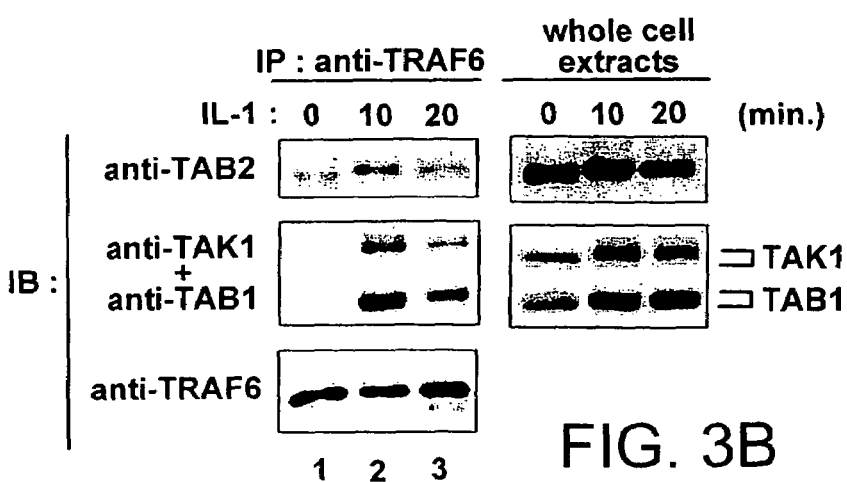

TRAF6 has been implicated in the IL-1 signaling pathway (Cao et al., Nature 383:443–446, 1996; Lomaga et al., Genes Dev. 13:1015–1024, 1999) and has been shown to complex with TAK1 (Ninomiya-Tsuji et al., Nature 398:252–256, 1999). The present inventors therefore determined whether TAB2 could interact with TRAF6 (FIG. 3A). T7-TAB2 was coexpressed with Flag-tagged TRAF6 in 293 cells and immunoprecipitated with anti-T7 antibody. The immune complexes were subjected to immunoblotting with a monoclonal antibody to Flag. TAB2 efficiently precipitated with TRAF6 (lane 4). To determine which domain of TAB2 is responsible for its TRAF6 association, the inventors tested whether TAB2N or TAB2C is able to bind to TRAF6, using the same experimental procedure. TRAF6 was found to coprecipitate with TAB2C but not TAB2N (lanes 6, 8). Thus, the C-terminal domain of TAB2 is required for TRAF6 binding.

We determined whether the interaction of TRAF6 and TAB2 occurred with physiological levels of these proteins (FIG. 3B). 293IL-1RI cells were treated with IL-1 or left untreated, and endogenous TRAF6 was immunoprecipitated with polyclonal antibodies to TRAF6. These immunoprecipitates were analyzed by immunoblotting with polyclonal antibodies to TAK1, TAB1 or TAB2. As observed previously (Ninomiya-Tsuji et al., Nature 398:252–256, 1999), endogenous TAK1 and TAB1 were coprecipitated with TRAF6 in an IL-1-dependent manner (middle panel). There was little association of endogenous TAB2 with TRAF6 in unstimulated cells. However, this association became evident upon IL-1 triggering, with a kinetic that was comparable with those of association of TAK1 and TAB1 with TRAF6 (upper panel). These results indicate that the association of endogenous TAK1, TAB1 and TAB2 with TRAF6 is ligand-dependent.

Figure 4A:
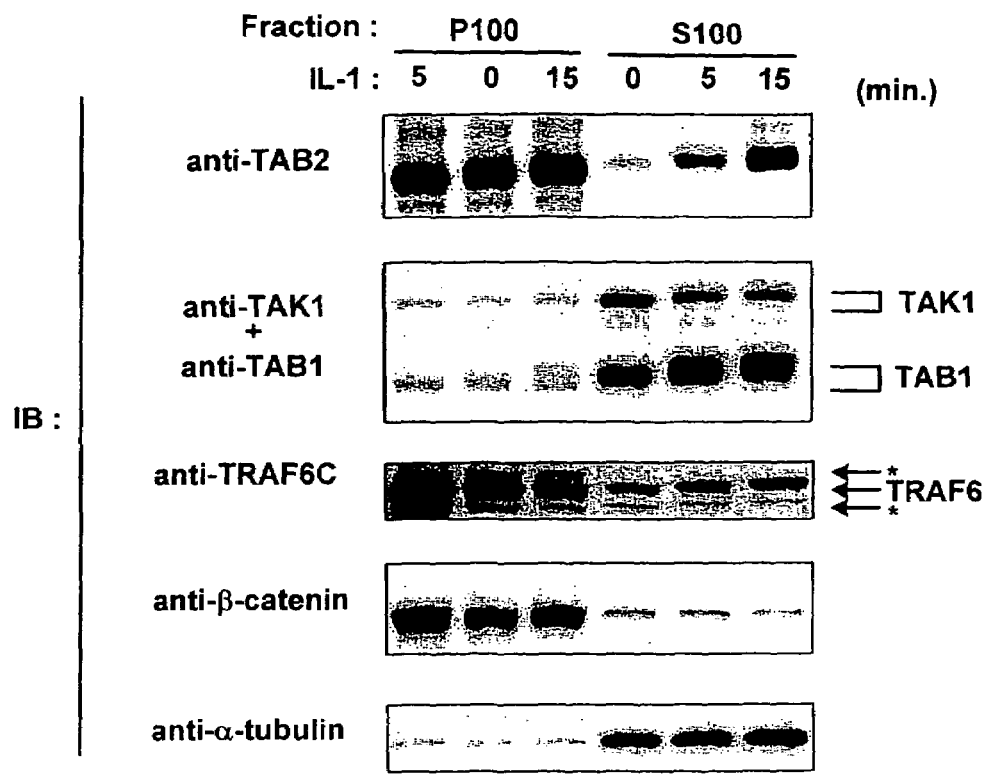

To further address how TAK1 and TAB2 interact with TRAF6 in an IL-1-dependent manner, the present inventors examined the subcellular distribution of these proteins under physiological conditions (FIG. 4A).

293IL-1RI cells at ~70% confluency were either left untreated or treated with IL-1 (10 ng/ml) for the indicated times, and were resuspended in 0.5 ml of ice-cold hypotonic buffer containing 10 mM HEPES (pH 7.4), 1.5 mM $MgCl_2$, 10 mM KCl, 0.2 mM PMSF, and 0.5 mM DTT and homogenized on ice with 30 strokes of a Dounce homogenizer. Unlysed cells, nuclei and cell debris were pelleted by centrifugation at 1,000 g for 5 min. Soluble [supernatant (S100)] (cytosol) and particulate [pellet (P100)] (membrane) fractions were generated centrifugation at 100,000 g for 1 hour. Samples were separated by SDS-PAGE, and immunoblotted with various antibodies as described above for the presence of TAK1, TAB1, TRAF6, and TAB2 proteins.

Western blot analysis revealed that the majority of TAK1 and TAB1 proteins was contained within the cytosolic fraction, whereas the TRAF6 proteins were located in both the membrane and cytosolic fractions. IL-1 stimulation did not change the localization patterns of TAK1, TAB1 or TRAF6. In contrast, the TAB2 proteins resided mostly in the membrane fraction in the absence of IL-1 stimulation. A significant fraction of the TAB2 proteins was directed to the cytosol following IL-1 stimulation.

Figure 4B:
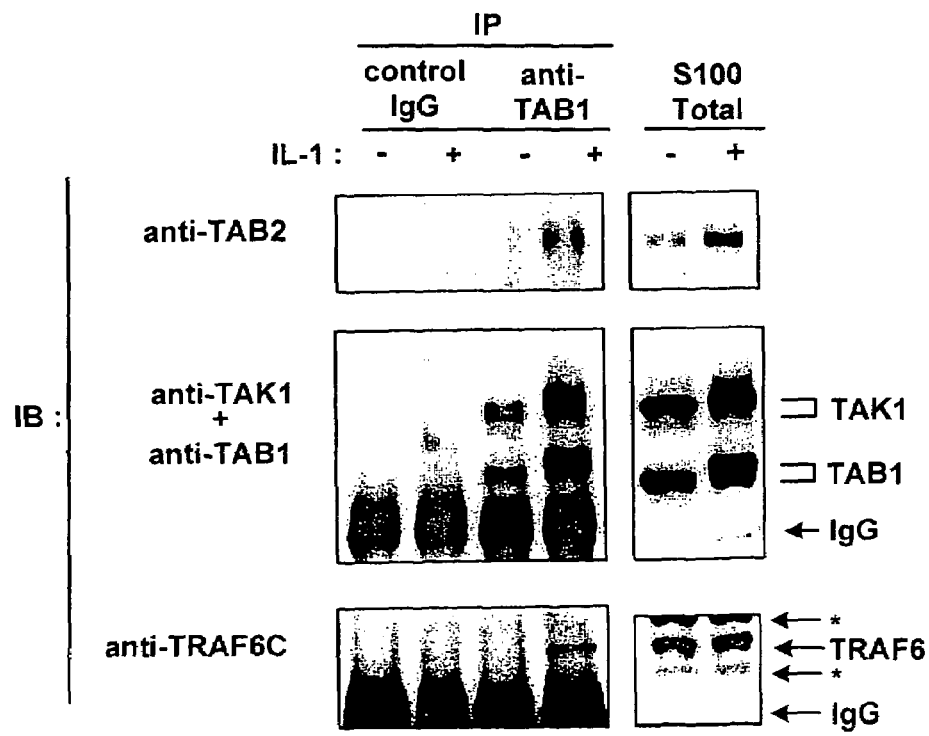

Immunoprecipitation using anti-TAB2 antibody was performed on cytosolic extracts, and the coprecipitation of endogenous TAK1 and TRAF6 proteins was determined by immunoblot analysis (FIG. 4B). There was a small or no association of TAB2 with TAK1 and TRAF6, respectively, in unstimulated cells. However, these interactions were dramatically increased upon IL-1 stimulation. Collectively, these findings suggest that IL-1 induces accumulation of TAB2 in the cytosol where TAB2 makes complexes with TRAF6 and TAK1.

Due to the intracellular fraction, it was demonstrated that TAB2 localizes mainly on membrane in the absence of IL-1. By IL-1 stimuli, TAB2 is released to cytoplasm and mediates the interaction between TRAF6 and TAK1 (FIG. 4). Since TAB2 does not have a domain that is presumed to interact with membrane, it may be linked to membrane by other molecule(s). Treatment with IL-1 will release TAB2 from such molecule(s) and then TAB2 will accumulate in cytoplasm. Therefore, the overexpression of TAB2 conceivably provides too abundant TAB2 to retain on membrane and then mimics the action of IL-1 ligand. Actually, the present inventors found that TAB2 accumulates in cytoplasm by overexpression of TAB2 even in the absence of IL-1 stimuli (data not shown). The overexpression of TAB2 mobilizes TRAF6 and TAK1 and induces a signal transduction cascade that leads to activation of JNK and NF-κB. Thus, redistribution of TAB2 protein by IL-1 stimuli is an important step involved in specification of TAK1. The inventors' data suggest that transition of TAB2 from membrane to cytoplasm is involved in specific and dynamic assembly of protein complex, and is an important step in which IL-1 signal is translated into activation of TAK1.

EXAMPLE 6

TAB2 Functions as an Adapter Protein for the Association of TAK1 with TRAF6

The above observations raise the possibility that TAB2 may function as an adapter protein for the association of TAK1 with TRAF6. If TAB2 functions as an adaptor between TRAF6 and TAK1, then overexpression of TRAF6 and TAK1 should reduce the amounts of TRAF6 coprecipitating with TAK1, given the limiting amounts of endogenous TAB2 in cells. To address this point, 293 cells were transfected with Flag-TRAF6 along with HA-TAK1 with or without T7-TAB2 (FIG. 5). There was a weak interaction between Flag-TRAF6 and HA-TAK1 (upper panel, lane 2). However, ectopic expression of TAB2 enhanced the coimmunoprecipitation of TRAF6 with TAK1 (upper panel, lane 4). These results are consistent with a model where TAB2 can form a ternary complex with TRAF6 and TAK1, facilitating the interaction of these proteins.

To further explore the biological basis for the significant inhibitory effects of TAB2C on IL-1 signaling, the present inventors examined the potential role of this region in the complex formation of TRAF6 and TAK1. T7-TAB2C was coexpressed with Flag-TRAF6 and HA-TAK1. The C-terminal domain of TAB2 was found to be sufficient for the interaction with either TAK1 or TRAF6 (FIGS. 1B and 3A). Consistent with this, TAB2C was coprecipitated with TAK1 (FIG. 5, middle panel, lane 6). However, overexpression of TAB2C did not enhance the association of TAK1 with TRAF6 (upper panel, lane 6). Thus, binary TAB2C-TRAF6 and TAB2C-TAK1 complexes are formed, but the whole structure of TAB2 is required for the formation of the ternary TRAF6-TAB2-TAK1 complex. The marked inhibitory effect of TAB2C in the IL-1 signaling assays likely derives from its ability to prevent the effective assembly of TRAF6 and TAK1. These results suggest that TAB2 is an intermediate signaling molecule linking TAK1 and TRAF6, and that this association may be required to transduce the IL-1 signal.

EXAMPLE 7

IL-1 Activates TAK1 Via Autophosphorylation

Figure 6A:
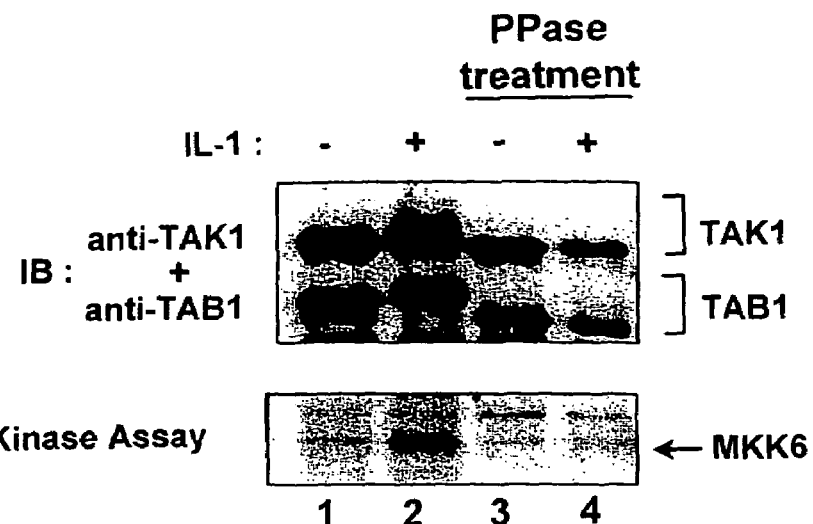

To address how TAK1 is activated following IL-1 stimulation, the present inventors analyzed endogenous TAK1 complexes in IL-1-treated and untreated cells (FIG. 6A). When 293IL-1RI cells were stimulated with IL-1, endogenous TAK1 was activated (lower panel, lanes 1, 2), as observed previously (Ninomiya-Tsuji et al., (1999) Nature, 398:252–256, 1999). Immunoblotting revealed that TAB1 coprecipitated with TAK1 in both IL-1-treated and untreated cells (upper panel, lanes 1, 2), suggesting that TAB1 constitutively associates with TAK1. However, TAK1 and TAB1 were found to migrate more slowly on SDS-PAGE when cells were treated with IL-1. Treatment with phosphatase eliminated these more slowly migrating bands (upper panel, lanes 3, 4), suggesting that they are the result of phosphorylation. Pre-treatment of the TAK1 complex with phosphatase abolished the ability of TAK1 to phosphorylate MKK6 (lower panel, lane 4), indicating that the dephosphorylation inactivates TAK1 kinase activity. Thus, phosphorylation of TAK1 is required for its catalytic activity. These results suggest that IL-1 activates TAK1 via phosphorylation of a pre-formed TAB1-TAK1 complex.

Figure 6B:
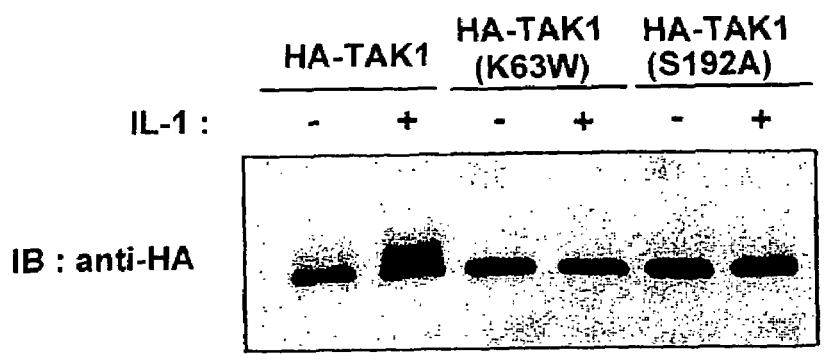

IL-1-induced phosphorylation of TAK1 could be mediated by another protein kinase or by autophosphorylation. These two possibilities can be distinguished by testing whether a catalytically inactive TAK1 mutant protein is phosphorylated upon IL-1 treatment. If another kinase is responsible for TAK1 phosphorylation, a catalytically inactive TAK1 should still be phosphorylated in response to IL-1. In contrast, if autophosphorylation is responsible for TAK1 phosphorylation, then the catalytically inactive TAK1 will not be phosphorylated. Results using the catalytically inactive mutant kinase, TAK1 (K63W) (above-mentioned), supported the latter possibility. Wild-type TAK1, but not TAK1 (K63W), was phosphorylated in response to IL-1 (FIG. 6B, lanes 1 to 4). These results demonstrate that TAK1 is autophosphorylated upon IL-1 treatment.

Figure 6D:
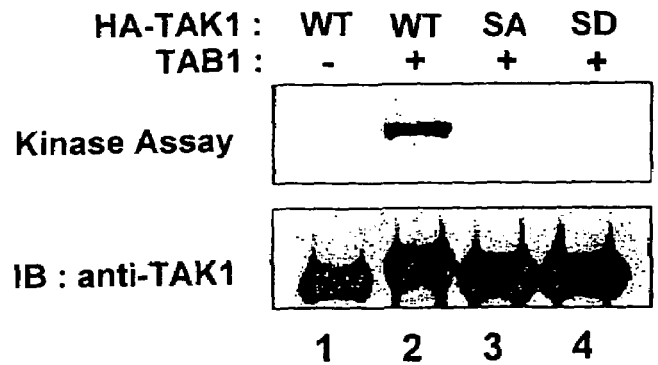

Phosphorylation of serine and/or threonine residues in the kinase activation loop between subdomains VII and VIII is essential for activation of many protein kinases, including MAPKKK (Johnson et al., Cell 85:149–158, 1996). The TAK1 Ser-192 residue located within the activation loop is also present in the MEKK1 and yeast SSK2 MAPKKKs (FIG. 6C). The MEKK1 Thr-1393 and SSK2 Thr-1460 are known to be essential for their activation via autophosphorylation (Deak et al., Biochem. J. 322:185–192, 1997). To address the question of whether the Ser-192 residue is involved in the regulation of TAK1 function, the present inventors generated a mutant TAK1 (S192A) in which Ser-192 was replaced with alanine. The TAK1 (S192A) mutant protein was not phosphorylated upon IL-1 treatment (FIG. 6B). Furthermore, in contrast to the wild type TAK1, the TAK1 (S192A) mutant had no kinase activity when coexpressed with TAB1 (FIG. 6D, lanes 2, 3). Thus, the Ser-192 residue of TAK1 is essential for TAK1 activity. These results suggest that Ser-192 in the activation loop of TAK1 plays a critical role in the activation of TAK1, probably as the site for autophosphorylation.

It has been shown for some kinases that replacing particular residues in the activation loop with negatively charged amino acids results in constitutive activation (Yan et al., J. Biol. Chem. 269:19067–19073, 1994; Ling et al., Proc. Natl. Acad. Sci. USA 95:3792–3797, 1998). The present inventors thus generated a mutant TAK1 (S192D) in which Ser-192 was replaced with aspartic acid, and compared its kinase activity to that of wild-type TAK1. The TAK1 (S192D) mutant exhibited no kinase activity, even when coexpressed together with TAB1 (FIG. 6D, lane 4). These results suggest that the molecular environment achieved by phosphorylation of Ser-192 in TAK1 cannot be mimicked by replacement with negatively charged residues.

TAK1 mutants, TAK1 (S192A) and TAK1 (S192D) (after-mentioned), containing a substitution of a serine residue in the activation loop were generated by PCR. First, a 5'-oligonucleotide (TTGTGGAGCTCCGGCAGTTG/SEQ ID NO:7) containing a SacI restriction site, together with 3'-oligonucleotides containing a NarI restriction site, (TTCAGGCGCCATCCAAGCAGCAGCCCC/SEQ ID NO:8) for TAK1(S192A) or (TTCAGGCGCCATCCAAG-CAGCATCCCC/SEQ ID NO:9) for TAK1 (S192D) were used to generate TAK1 mutants fragments. The resulting SacI-NarI fragment were subcloned into the SacI and NarI sites of pSP72-HA-TAK1 which contains an N-terminal HA epitope-tagged full length of TAK1 cDNA fragment in the EcoRI and BamHI sites of the vector pSP72 (Promega). Next, the EcoRI-BamHI TAK1 mutant fragment was cloned into the EcoRI-BamHI gap of the pEF vector to generate pEF-HA-TAK1 mutants. All constructs were verified by DNA sequencing.

Activation of many MAPKKKs are regulated by phosphorylation (Herskowitz, Cell 80:187–197, 1995; Deak et l., Biochem. J. 322:185–192, 1997; Siow et al., J. Biol. Chem. 272:7586–7594, 1997; King et al., Nature 396:180–183, 1998; Leung et al., J. Biol. Chem. 273:32408–32415, 1998; Posas et al., EMBO J. 17:1385–1394, 1998). Phosphorylation of some MAPKKKs is mediated by other protein kinases, such as Ste20-like MAPKKKKs. In other cases, autophosphorylation is implicated in the activation of MAPKKKs. The results presented here demonstrate that autophosphorylation of TAK1 is important for IL-1-induced activation of TAK1. Mutation to alanine of the Ser-192 that lies in the activation loop between subdomains VII and VIII abolishes IL-1-induced phosphorylation of TAK1. Furthermore, this mutation generates a kinase-inactive form of TAK1. Based on these results, it is likely that Ser-192 is the site of TAK1 autophosphorylation and is critical for its catalytic activity.

Autophosphorylation of a kinase is mediated by either an inter- or intra-molecular reaction. One common example of inter-molecular autophosphorylation is the activation of receptor tyrosine kinases. Upon ligand binding, these receptors form homodimers and phosphorylate their dimerized partner, resulting in activation of the kinase. Similar mechanisms of activation were described for such MAPKKKs as ASK1 and MLK3. In response to upstream stimuli, both MLK3 and ASK1 form homodimers and are consequently activated. On the other hand, the present inventors found that TAK1 autophosphorylation occurs by an intra-molecular reaction (data not shown), suggesting that dimerization might not be a critical step for TAK1 activation. Consistent with this, the inventors could not detect dimerization of TAK1 by coimmunoprecipitation assay (data not shown). These findings are similar to recent reports that intra-molecular autophosphorylation is crucial for activation of MEKKI and SSK2 (Deak et al., Biochem. J. 322:185–192, 1997; Siow et al., J. Biol. Chem. 272:7586–7594, 1997). The potential autophosphorylation sites of TAK1, MEKK1 and SSK2 are present at homologous positions within their activation loops. In the case of TAK1, TAB1 is required for autophosphorylation and activation. Interestingly, autophosphorylation of SSK2 also requires an interacting protein SSK1, which functions as an upstream regulator of SSK2 (Posas et al., EMBO J. 17:1385–1394, 1998). Thus, TAK1, SSK2 and possibly MEKK1 may be regulated by a common activation mechanism. Collectively, these observations suggest that there are at least two different mechanisms for MAPKKKs activation that involve autophosphorylation, namely dimerization-induced inter-molecular autophosphorylation and regulator-dependent intra-molecular autophosphorylation.

INDUSTRIAL APPLICABILITY

The present invention demonstrated that, in signal transduction of IL-1, TAB2 acts as an adaptor that provides bridges between TRAF6 and TAK1. Also, it was revealed that partial peptides of C-terminal of TAB2 act as inhibitors of IL-1 signal transduction. The screening method of the present invention enables isolating compounds for inhibiting IL-1 signal transduction specifically through the inhibition of signal transduction by TRAF6, TAK1, or TAB2. It is believed that such compounds show anti-inflammatory action by inhibiting signal transduction of IL-1. Therefore, such a compound is an important candidate for a novel medicament against various diseases and injury associated with inflammation.

What is claimed is:

1. An isolated nucleic acid encoding a polypeptide comprising the amino acid sequence of SEQ ID NO:2.

2. A vector comprising the nucleic acid of claim 1.

3. A host cell harboring the nucleic acid of claim 1.

4. A host cell harboring the vector of claim 2.

5. A method for producing a polypeptide, the method comprising: culturing the host cell of claim 4, and recovering from the host cell, or the culture supernatant thereof, the polypeptide comprising SEQ ID NO:2.

6. A method of screening for a compound that inhibits signal transduction of IL-1, comprising the steps of:
 (a) contacting a polypeptide encoded by the nucleic acid of claim 1 with TAK1 or TRAF6, in the presence of a test compound;
 (b) detecting binding between the polypeptide and TAK1 or TRAF6; and
 (c) identifying a test compound as compound that inhibits signal transduction of IL-1 if the test compound inhibits binding between the polypeptide and TAK1 or TRAF6, compared to binding in the absence of the test compound.

7. The method according to claim 6, wherein the detecting in step (b) is carried out by immunoprecipitation.

8. A method of screening for a compound that inhibits signal transduction of IL-1, comprising the steps of:
 (a) contacting a mammalian cell that expresses a polypeptide encoded by the nucleic acid of claim 1 with IL-1, in the presence of a test compound;
 (b) detecting a biological activity that is transduced by the polypeptide, wherein said biological activity is selected from the group consisting of activation of TAK1, activation of NF-κB, activation of JNK, translocation of TAB2 protein from cell membrane to cytoplasm, and autophosphorylation of TAK1; and
 (c) identifying a test compound as a compound that inhibits signal transduction of IL-1 if the test compound inhibits the biological activity compared to the biological activity in the absence of the test compound.

9. The method according to claim 8, wherein the biological activity is activation of TAK1.

10. The method according to claim 9, wherein activation of TAK1 is detected by detecting phosphorylation of MKK6.

11. The method according to claim 8, wherein the biological activity is activation of NF-κB.

12. The method according to claim 11, wherein activation of NF-κB is detected by detecting expression of a reporter gene in the cell, wherein the cell harbors a vector that comprises a reporter gene that binds downstream of an Ig-κ promoter.

13. The method according to claim 8, wherein the biological activity is activation of JNK.

14. The method according to claim 13, wherein activation of JNK is detected by detecting phosphorylation of Jun.

15. The method according to claim 8, wherein the biological activity is translocation of the polypeptide from the cell membrane to the cytoplasm.

16. The method according to claim 8, wherein the biological activity is autophosphorylation of TAK1.

17. The method according to claim 8, wherein the cell comprises an expression vector that directs expression of the polypeptide.

18. The method according to claim 9, wherein the cell comprises an expression vector that directs expression of the polypeptide.

19. The method according to claim 10, wherein the cell comprises an expression vector that directs expression of the polypeptide.

20. The method according to claim 11, wherein the cell comprises an expression vector that directs expression of the polypeptide.

21. The method according to claim 12, wherein the cell comprises an expression vector that directs expression of the polypeptide.

22. The method according to claim 13, wherein the cell comprises an expression vector that directs expression of the polypeptide.

23. The method according to claim 14, wherein the cell comprises an expression vector that directs expression of the polypeptide.

24. The method according to claim 15, wherein the cell comprises an expression vector that directs expression of the polypeptide.

25. The method according to claim 16, wherein the cell comprises an expression vector that directs expression of the polypeptide.

26. An agent that inhibits signal transduction of IL-1, IL-18 or LPS, said agent comprising, as an active ingredient, the nucleic acid encoding TAB2N (residues 1–400 of SEQ ID NO:2) or TAB2C (residues 401–693 of SEQ ID NO:2).

27. The nucleic acid of claim 1 wherein the polypeptide consists of SEQ ID NO:2.

28. The nucleic acid of claim 1 wherein the polypeptide is a fusion protein comprising SEQ ID NO:2.

29. The nucleic acid of claim 28 wherein the fusion protein comprises a peptide or protein selected from the group consisting of FLAG, 6×His, 10×His, glutathione-S-transferase, influenza agglutinin, immunoglobulin constant region, β-galactosidase, and maltose-binding protein.

30. A vector comprising the nucleic acid of claim 27.

31. A host cell comprising the nucleic acid of claim 27.

32. A host cell comprising the vector of claim 30.

33. A method for producing a polypeptide, comprising culturing the host cell of claim 32 and recovering from the host cell, or the culture supernatant thereof, the polypeptide encoded by the nucleic acid.

34. An isolated nucleic acid comprising the coding region of SEQ ID NO:1.

35. The nucleic acid of claim 34 consisting of the coding region of SEQ ID NO:1.

36. A vector comprising the nucleic acid of claim 34.

37. A host cell comprising the nucleic acid of claim 34.

38. A host cell comprising the vector of claim 36.

39. A method for producing a polypeptide, comprising culturing the host cell of claim 38 and recovering from the host cell, or the culture supernatant thereof, the polypeptide encoded by SEQ ID NO:1.

40. An isolated nucleic acid encoding a polypeptide that comprises SEQ ID NO:2 in which up to 100 amino acids are substituted, deleted, and/or inserted, wherein said polypeptide mediates IL-1 signal transduction, inhibits IL-1 signal transduction, or binds to TAK1 or TRAF6.

41. The nucleic acid of claim 40, wherein up to 50 amino acids are substituted, deleted, and/or inserted.

42. The nucleic acid of claim 40, wherein up to 20 amino acids are substituted, deleted, and/or inserted.

43. The nucleic acid of claim 40, wherein up to 10 amino acids are substituted, deleted, and/or inserted.

44. The nucleic acid of claim 40, wherein up to 5 amino acids are substituted, deleted, and/or inserted.

45. The nucleic acid of claim 40, wherein up to 3 amino acids are substituted, deleted, and/or inserted.

46. A vector comprising the nucleic acid of claim 40.

47. A host cell comprising the nucleic acid of claim 40.

48. A host cell comprising the vector of claim 46.

49. A method for producing a polypeptide, comprising culturing the host cell of claim 48 and recovering from the host cell, or the culture supernatant thereof, the polypeptide encoded by the nucleic acid.

50. An isolated nucleic acid that hybridizes, after washing with 0.1×SSC and 0.1% SDS at 600° C., with a nucleic acid probe consisting of the complement of SEQ ID NO:1, wherein said nucleic acid encodes a polypeptide that mediates IL-1 signal transduction.

51. A vector comprising the nucleic acid of claim 50.

52. A host cell comprising the nucleic acid of claim 50.

53. A host cell comprising the vector of claim 51.

54. A method for producing a polypeptide, comprising culturing the host cell of claim 53 and recovering from the host cell, or the culture supernatant thereof, the polypeptide encoded by the nucleic acid.

55. An isolated nucleic acid encoding a polypeptide comprising a fragment of SEQ ID NO:2, wherein the polypeptide mediates IL-1 signal transduction.

56. An isolated nucleic acid encoding TAB2N (residues 1–400 of SEQ ID NO:2) or TAB2C (residues 401–693 of SEQ ID NO:2).

57. A vector comprising the nucleic acid of claim 55.

58. A host cell comprising the nucleic acid of claim 55.

59. A host cell comprising the vector of claim 57.

60. A method for producing a polypeptide, comprising culturing the host cell of claim 59 and recovering from the host cell, or the culture supernatant thereof, the polypeptide encoded by the nucleic acid.

61. An isolated nucleic acid encoding a polypeptide that comprises a sequence at least 80% identical to SEQ ID NO:2, wherein the polypeptide mediates IL-1 signal transduction, inhibits IL-1 signal transduction, or binds to TAK1 or TRAF6.

62. The nucleic acid of claim 61 wherein the sequence is at least 90% identical to SEQ ID NO:2.

63. The nucleic acid of claim 61 wherein the sequence is at least 95% identical to SEQ ID NO:2.

64. The nucleic acid of claim 61 wherein the sequence is at least 98% identical to SEQ ID NO:2.

65. A vector comprising the nucleic acid of claim 61.

66. A host cell comprising the nucleic acid of claim 61.

67. A host cell comprising the vector of claim 65.

68. A method for producing a polypeptide, comprising culturing the host cell of claim 67 and recovering from the host cell, or the culture supernatant thereof, the polypeptide encoded by the nucleic acid.

69. An agent that inhibits signal transduction of IL-1, IL-18 or LPS, said agent comprising, as an active ingredient, the nucleic acid of claim 61.

* * * * *

UNITED STATES PATENT AND TRADEMARK OFFICE
CERTIFICATE OF CORRECTION

PATENT NO. : 7,153,664 B2
APPLICATION NO. : 10/151569
DATED : December 26, 2006
INVENTOR(S) : Kunihiro Matsumoto It is certified that error appears in the above-identified patent and that said Letters Patent is hereby corrected as shown below:

On the title page insert:
-- (63) Continuation-in-part of application No. PCT/JP99/06466, filed Nov. 19, 1999. --.

Column 1, before the section "TECHNICAL FIELD", insert:
-- This application is a continuation-in-part of and claims the benefit of priority under 35 U.S.C. § 120 of PCT/JP99/06466, filed November 19, 1999. The contents of the prior application are thereby incorporated by reference in their entirety. --.

Column 62, line 24, "the nucleic acid encoding TAB2N (residues 1-400of"
should read -- a nucleic acid encoding TAB2N (residues 1-400 of --.

Column 63, line 9, "600°C."
should read -- 60°C --.

Signed and Sealed this

Twenty-seventh Day of July, 2010

David J. Kappos
*Director of the United States Patent and Trademark Office*

SEQUENCE LISTING

```
<160> NUMBER OF SEQ ID NOS: 19

<210> SEQ ID NO 1
<211> LENGTH: 2787
<212> TYPE: DNA
<213> ORGANISM: Homo sapiens
<220> FEATURE:
<221> NAME/KEY: CDS
<222> LOCATION: (81)...(2159)

<400> SEQUENCE: 1
gaattcgtga gatgagtact atttccacta aggcctagaa ttgcctactg tacaaatagt        60
cctgatcagg caatatacga atg gcc caa gga agc cac caa att gat ttt cag      113
                         Met Ala Gln Gly Ser His Gln Ile Asp Phe Gln
                           1               5                  10 gtt tta cat gac ctg cga caa aaa ttc cct gaa gta cct gaa gtt gtt        161
Val Leu His Asp Leu Arg Gln Lys Phe Pro Glu Val Pro Glu Val Val
             15                  20                  25 gta tcc agg tgc atg tta cag aat aat aat aac ctg gat gcc tgc tgt        209
Val Ser Arg Cys Met Leu Gln Asn Asn Asn Asn Leu Asp Ala Cys Cys
         30                  35                  40 gct gtt ctc tct cag gag agt aca aga tat ctt tat ggt gaa gga gac        257
Ala Val Leu Ser Gln Glu Ser Thr Arg Tyr Leu Tyr Gly Glu Gly Asp
     45                  50                  55 ttg aat ttt tca gat gat tct gga att tct ggt cta cgc aat cac atg        305
Leu Asn Phe Ser Asp Asp Ser Gly Ile Ser Gly Leu Arg Asn His Met
 60                  65                  70                  75 act tct ctc aac ttg gac ttg caa tca cag aac att tac cac cat gga        353
Thr Ser Leu Asn Leu Asp Leu Gln Ser Gln Asn Ile Tyr His His Gly
                 80                  85                  90 aga gaa gga agt aga atg aat gga agt agg act cta acg cac agc att        401
Arg Glu Gly Ser Arg Met Asn Gly Ser Arg Thr Leu Thr His Ser Ile
             95                 100                 105 agt gat gga caa ctt caa ggt ggc cag tcc aat agt gaa cta ttt cag        449
Ser Asp Gly Gln Leu Gln Gly Gly Gln Ser Asn Ser Glu Leu Phe Gln
         110                 115                 120 cag gag cca cag aca gca cca gct caa gtt cct caa ggc ttt aat gtt        497
Gln Glu Pro Gln Thr Ala Pro Ala Gln Val Pro Gln Gly Phe Asn Val
     125                 130                 135
```

-continued

```
ttt gga atg tcc agt tcc tct ggt gct tca aat tca gca cca cat ctt        545
Phe Gly Met Ser Ser Ser Ser Gly Ala Ser Asn Ser Ala Pro His Leu
140                 145                 150                 155 gga ttt cac tta ggc agc aaa gga aca tct agc ctt tct caa caa act        593
Gly Phe His Leu Gly Ser Lys Gly Thr Ser Ser Leu Ser Gln Gln Thr
                160                 165                 170 ccc aga ttt aat ccc att atg gta act tta gcc cca aat atc cag act        641
Pro Arg Phe Asn Pro Ile Met Val Thr Leu Ala Pro Asn Ile Gln Thr
            175                 180                 185 ggt cgt aat act cct aca tct ttg cac ata cat ggt gta cct cca cct        689
Gly Arg Asn Thr Pro Thr Ser Leu His Ile His Gly Val Pro Pro Pro
        190                 195                 200 gta ctt aac agt cca cag gga aat tct atc tat att agg cct tac att        737
Val Leu Asn Ser Pro Gln Gly Asn Ser Ile Tyr Ile Arg Pro Tyr Ile
    205                 210                 215 aca act cct ggt ggt aca act cga cag aca caa cag cat tct ggc tgg        785
Thr Thr Pro Gly Gly Thr Thr Arg Gln Thr Gln Gln His Ser Gly Trp
220                 225                 230                 235 gta tct cag ttt aat ccc atg aac cct cag caa gtt tat cag cct tca        833
Val Ser Gln Phe Asn Pro Met Asn Pro Gln Gln Val Tyr Gln Pro Ser
                240                 245                 250 cag cct ggt ccc tgg act act tgt cct gca tct aat cct ctg tca cat        881
Gln Pro Gly Pro Trp Thr Thr Cys Pro Ala Ser Asn Pro Leu Ser His
            255                 260                 265 acc tca tct caa cag cca aat cag caa ggc cac cag acc tct cat gtc        929
Thr Ser Ser Gln Gln Pro Asn Gln Gln Gly His Gln Thr Ser His Val
        270                 275                 280 tac atg cca atc agt tca cct act act tca caa cca cca acc att cat        977
Tyr Met Pro Ile Ser Ser Pro Thr Thr Ser Gln Pro Pro Thr Ile His
    285                 290                 295 tca tct ggt agc tca cag tct tct gcc cat agc caa tat aac att cag       1025
Ser Ser Gly Ser Ser Gln Ser Ser Ala His Ser Gln Tyr Asn Ile Gln
300                 305                 310                 315 aat att tca aca gga cct cga aaa aac cag att gaa atc aaa ctt gaa       1073
Asn Ile Ser Thr Gly Pro Arg Lys Asn Gln Ile Glu Ile Lys Leu Glu
                320                 325                 330 ccc cca caa aga aat aat tct tca aaa ctg cgt tct tct gga cct cga       1121
Pro Pro Gln Arg Asn Asn Ser Ser Lys Leu Arg Ser Ser Gly Pro Arg
            335                 340                 345 acc tcc agc act tcc tct tca gtc aat agc cag acc tta aac aga aat       1169
Thr Ser Ser Thr Ser Ser Ser Val Asn Ser Gln Thr Leu Asn Arg Asn
        350                 355                 360 cag ccc act gtt tac ata gct gcc agc ccc cca aat acg gat gag ctg       1217
Gln Pro Thr Val Tyr Ile Ala Ala Ser Pro Pro Asn Thr Asp Glu Leu
    365                 370                 375 atg tcc cgt agt caa cct aag gtc tat att tca gcg aat gct gcc aca       1265
Met Ser Arg Ser Gln Pro Lys Val Tyr Ile Ser Ala Asn Ala Ala Thr
380                 385                 390                 395 gga gat gaa cag gtc atg cgg aat cag ccc aca ctc ttc ata tcc aca       1313
Gly Asp Glu Gln Val Met Arg Asn Gln Pro Thr Leu Phe Ile Ser Thr
                400                 405                 410 aac tct gga gca tct gct gcc tcc agg aac atg tct ggg caa gtg agc       1361
Asn Ser Gly Ala Ser Ala Ala Ser Arg Asn Met Ser Gly Gln Val Ser
            415                 420                 425 atg ggt cct gcc ttt att cat cac cat cct ccc aaa agt cga gca ata       1409
Met Gly Pro Ala Phe Ile His His His Pro Pro Lys Ser Arg Ala Ile
        430                 435                 440 ggc aat aac tct gca acc tct cct cga gtg gta gtc act cag ccc aat       1457
Gly Asn Asn Ser Ala Thr Ser Pro Arg Val Val Val Thr Gln Pro Asn
```

```
                    445                 450                 455
acg aaa tac act ttc aaa att aca gtc tct ccc aat aag ccc cct gca      1505
Thr Lys Tyr Thr Phe Lys Ile Thr Val Ser Pro Asn Lys Pro Pro Ala
460                 465                 470                 475 gtt tca cca ggg gtg gtg tcc cct acc ttt gaa ctt aca aat ctt ctt      1553
Val Ser Pro Gly Val Val Ser Pro Thr Phe Glu Leu Thr Asn Leu Leu
                480                 485                 490 aat cat cct gat cat tat gta gaa acc gag aat att cag cac ctc acg      1601
Asn His Pro Asp His Tyr Val Glu Thr Glu Asn Ile Gln His Leu Thr
            495                 500                 505 gac cct aca tta gca cat gtg gat aga ata agt gaa aca cgg aaa ctg      1649
Asp Pro Thr Leu Ala His Val Asp Arg Ile Ser Glu Thr Arg Lys Leu
        510                 515                 520 agt atg gga tct gat gat gct gcc tac aca caa gct ctt ttg gta cac      1697
Ser Met Gly Ser Asp Asp Ala Ala Tyr Thr Gln Ala Leu Leu Val His
    525                 530                 535 cag aag gcc aga atg gaa cga ctt caa aga gaa ctt gag att caa aag      1745
Gln Lys Ala Arg Met Glu Arg Leu Gln Arg Glu Leu Glu Ile Gln Lys
540                 545                 550                 555 aaa aag ctg gat aaa tta aaa tct gag gtt aat gaa atg gaa aat aat      1793
Lys Lys Leu Asp Lys Leu Lys Ser Glu Val Asn Glu Met Glu Asn Asn
                560                 565                 570 cta act cga agg cgc ctg aaa aga tca aat tct ata tcc cag ata cct      1841
Leu Thr Arg Arg Arg Leu Lys Arg Ser Asn Ser Ile Ser Gln Ile Pro
            575                 580                 585 tcc ctt gaa gaa atg cag cag ctg aga agt tgt aat aga caa ctc cag      1889
Ser Leu Glu Glu Met Gln Gln Leu Arg Ser Cys Asn Arg Gln Leu Gln
        590                 595                 600 att gac att gac tgc tta acc aaa gaa att gat ctt ttt caa gcc cga      1937
Ile Asp Ile Asp Cys Leu Thr Lys Glu Ile Asp Leu Phe Gln Ala Arg
    605                 610                 615 gga cca cat ttt aac ccc agc gct att cat aac ttt tat gac aat att      1985
Gly Pro His Phe Asn Pro Ser Ala Ile His Asn Phe Tyr Asp Asn Ile
620                 625                 630                 635 gga ttt gta ggt cct gtg cca cca aaa ccc aaa gat caa agg tcc atc      2033
Gly Phe Val Gly Pro Val Pro Pro Lys Pro Lys Asp Gln Arg Ser Ile
                640                 645                 650 atc aaa aca cca aag act caa gac aca gaa gat gat gag gga gct cag      2081
Ile Lys Thr Pro Lys Thr Gln Asp Thr Glu Asp Asp Glu Gly Ala Gln
            655                 660                 665 tgg aat tgt acc gcc tgt act ttt ttg aac cat cca gcc tta att cgc      2129
Trp Asn Cys Thr Ala Cys Thr Phe Leu Asn His Pro Ala Leu Ile Arg
        670                 675                 680 tgt gaa cag tgt gag atg cca agg cat ttc tgagccaaat ggccctgtat        2179
Cys Glu Gln Cys Glu Met Pro Arg His Phe
    685                 690 cttctctaaa accacatcta aagttcaaga aactagtctg tcatcgggaa aaagtttcac    2239
tgctacatag gattttgtca aattgaaggt gtgacaagat ggtgttctgc taatgttaaa    2299
tgtcagccca cagagctaat aatacctcag tataatgtca tgagcagttg aaattcatca    2359
catgaaaagt aatctgctga aagacttggt tgcccactgc ctaactgtgt acagtgttac    2419
cagtgtccca ttatggataa ttctcaatat gttaacacct aggtgttccc aatacctttt    2479
tcccctcatg tcactactga attttgacag gaggaaggaa tagaatgata gcttgtttta    2539
tttgtaaagc tttcagtgaa acactacata cacgaagaaa aggaacaagg tttaactatt    2599
taagaaccat ttgctgccgc atagtgccat tggatagggg agaacttcag aaatctgtgg    2659
tactcttggc cttgtctttg tcttccctga acgtgtctcc actctgtgaa gccagcatct    2719
```

```
agggggctaaa gatgcaaagg aaagcagcat gcattgtctg tacaaatgtg cagcgaaatc   2779
cggaattc                                                              2787
```

<210> SEQ ID NO 2
<211> LENGTH: 693
<212> TYPE: PRT
<213> ORGANISM: Homo sapiens

<400> SEQUENCE: 2

```
Met Ala Gln Gly Ser His Gln Ile Asp Phe Gln Val Leu His Asp Leu
 1               5                  10                  15

Arg Gln Lys Phe Pro Glu Val Pro Glu Val Val Ser Arg Cys Met
                20                  25                  30

Leu Gln Asn Asn Asn Leu Asp Ala Cys Cys Ala Val Leu Ser Gln
         35                  40                  45

Glu Ser Thr Arg Tyr Leu Tyr Gly Glu Gly Asp Leu Asn Phe Ser Asp
    50                  55                  60

Asp Ser Gly Ile Ser Gly Leu Arg Asn His Met Thr Ser Leu Asn Leu
65                  70                  75                  80

Asp Leu Gln Ser Gln Asn Ile Tyr His His Gly Arg Glu Gly Ser Arg
                85                  90                  95

Met Asn Gly Ser Arg Thr Leu Thr His Ser Ile Ser Asp Gly Gln Leu
            100                 105                 110

Gln Gly Gly Gln Ser Asn Ser Glu Leu Phe Gln Gln Glu Pro Gln Thr
        115                 120                 125

Ala Pro Ala Gln Val Pro Gln Gly Phe Asn Val Phe Gly Met Ser Ser
    130                 135                 140

Ser Ser Gly Ala Ser Asn Ser Ala Pro His Leu Gly Phe His Leu Gly
145                 150                 155                 160

Ser Lys Gly Thr Ser Ser Leu Ser Gln Gln Thr Pro Arg Phe Asn Pro
                165                 170                 175

Ile Met Val Thr Leu Ala Pro Asn Ile Gln Thr Gly Arg Asn Thr Pro
            180                 185                 190

Thr Ser Leu His Ile His Gly Val Pro Pro Val Leu Asn Ser Pro
        195                 200                 205

Gln Gly Asn Ser Ile Tyr Ile Arg Pro Tyr Ile Thr Thr Pro Gly Gly
    210                 215                 220

Thr Thr Arg Gln Thr Gln Gln His Ser Gly Trp Val Ser Gln Phe Asn
225                 230                 235                 240

Pro Met Asn Pro Gln Gln Val Tyr Gln Pro Ser Gln Pro Gly Pro Trp
                245                 250                 255

Thr Thr Cys Pro Ala Ser Asn Pro Leu Ser His Thr Ser Ser Gln Gln
            260                 265                 270

Pro Asn Gln Gln Gly His Gln Thr Ser His Val Tyr Met Pro Ile Ser
        275                 280                 285

Ser Pro Thr Thr Ser Gln Pro Pro Thr Ile His Ser Ser Gly Ser Ser
    290                 295                 300

Gln Ser Ser Ala His Ser Gln Tyr Asn Ile Gln Asn Ile Ser Thr Gly
305                 310                 315                 320

Pro Arg Lys Asn Gln Ile Glu Ile Lys Leu Glu Pro Pro Gln Arg Asn
                325                 330                 335

Asn Ser Ser Lys Leu Arg Ser Ser Gly Pro Arg Thr Ser Ser Thr Ser
            340                 345                 350
```

```
Ser Ser Val Asn Ser Gln Thr Leu Asn Arg Asn Gln Pro Thr Val Tyr
        355                 360                 365
Ile Ala Ala Ser Pro Pro Asn Thr Asp Glu Leu Met Ser Arg Ser Gln
    370                 375                 380
Pro Lys Val Tyr Ile Ser Ala Asn Ala Ala Thr Gly Asp Glu Gln Val
385                 390                 395                 400
Met Arg Asn Gln Pro Thr Leu Phe Ile Ser Thr Asn Ser Gly Ala Ser
                405                 410                 415
Ala Ala Ser Arg Asn Met Ser Gly Gln Val Ser Met Gly Pro Ala Phe
            420                 425                 430
Ile His His Pro Pro Lys Ser Arg Ala Ile Gly Asn Asn Ser Ala
        435                 440                 445
Thr Ser Pro Arg Val Val Thr Gln Pro Asn Thr Lys Tyr Thr Phe
    450                 455                 460
Lys Ile Thr Val Ser Pro Asn Lys Pro Ala Val Ser Pro Gly Val
465                 470                 475                 480
Val Ser Pro Thr Phe Glu Leu Thr Asn Leu Leu Asn His Pro Asp His
                485                 490                 495
Tyr Val Glu Thr Glu Asn Ile Gln His Leu Thr Asp Pro Thr Leu Ala
            500                 505                 510
His Val Asp Arg Ile Ser Glu Thr Arg Lys Leu Ser Met Gly Ser Asp
        515                 520                 525
Asp Ala Ala Tyr Thr Gln Ala Leu Leu Val His Gln Lys Ala Arg Met
    530                 535                 540
Glu Arg Leu Gln Arg Glu Leu Glu Ile Gln Lys Lys Leu Asp Lys
545                 550                 555                 560
Leu Lys Ser Glu Val Asn Glu Met Glu Asn Asn Leu Thr Arg Arg Arg
                565                 570                 575
Leu Lys Arg Ser Asn Ser Ile Ser Gln Ile Pro Ser Leu Glu Glu Met
            580                 585                 590
Gln Gln Leu Arg Ser Cys Asn Arg Gln Leu Gln Ile Asp Ile Asp Cys
        595                 600                 605
Leu Thr Lys Glu Ile Asp Leu Phe Gln Ala Arg Gly Pro His Phe Asn
    610                 615                 620
Pro Ser Ala Ile His Asn Phe Tyr Asp Asn Ile Gly Phe Val Gly Pro
625                 630                 635                 640
Val Pro Pro Lys Pro Lys Asp Gln Arg Ser Ile Ile Lys Thr Pro Lys
                645                 650                 655
Thr Gln Asp Thr Glu Asp Asp Glu Gly Ala Gln Trp Asn Cys Thr Ala
            660                 665                 670
Cys Thr Phe Leu Asn His Pro Ala Leu Ile Arg Cys Glu Gln Cys Glu
        675                 680                 685
Met Pro Arg His Phe
    690

<210> SEQ ID NO 3
<211> LENGTH: 30
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 3
tataacattc agaatatttc aacaggacct                                    30
```

```
<210> SEQ ID NO 4
<211> LENGTH: 30
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 4
caggtcgact cactgttcat ctcctgtggc                                      30

<210> SEQ ID NO 5
<211> LENGTH: 30
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 5
cgcgaattca tgcggaatca gcccacactc                                      30

<210> SEQ ID NO 6
<211> LENGTH: 30
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 6
cccctggtga aactgcaggg ggcttattgg                                      30

<210> SEQ ID NO 7
<211> LENGTH: 20
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 7
ttgtggagct ccggcagttg                                                 20

<210> SEQ ID NO 8
<211> LENGTH: 27
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 8
ttcaggcgcc atccaagcag cagcccc                                         27

<210> SEQ ID NO 9
<211> LENGTH: 27
<212> TYPE: DNA
<213> ORGANISM: Artificial Sequence
<220> FEATURE:
<223> OTHER INFORMATION: Artificially Synthesized Oligonucleotide
      Sequence

<400> SEQUENCE: 9
ttcaggcgcc atccaagcag catcccc                                         27
```

-continued

```
<210> SEQ ID NO 10
<211> LENGTH: 25
<212> TYPE: PRT
<213> ORGANISM: Homo sapiens

<400> SEQUENCE: 10

Asp Phe Gly Thr Ala Cys Asp Ile Gln Thr His Met Thr Asn Asn Lys
1               5                   10                  15

Gly Ser Ala Ala Trp Met Ala Pro Glu
            20                  25

<210> SEQ ID NO 11
<211> LENGTH: 32
<212> TYPE: PRT
<213> ORGANISM: Homo sapiens

<400> SEQUENCE: 11

Asp Phe Gly Ala Ala Ala Arg Leu Ala Ser Lys Gly Thr Gly Ala Gly
1               5                   10                  15

Glu Phe Gln Gly Gln Leu Leu Gly Thr Ile Ala Phe Met Ala Pro Glu
            20                  25                  30

<210> SEQ ID NO 12
<211> LENGTH: 31
<212> TYPE: PRT
<213> ORGANISM: Homo sapiens

<400> SEQUENCE: 12

Asp Phe Gly Ala Ser Lys Arg Leu Gln Thr Ile Cys Leu Ser Gly Thr
1               5                   10                  15

Gly Met Lys Ser Val Thr Gly Thr Pro Tyr Trp Met Ser Pro Glu
            20                  25                  30

<210> SEQ ID NO 13
<211> LENGTH: 31
<212> TYPE: PRT
<213> ORGANISM: Homo sapiens

<400> SEQUENCE: 13

Asp Phe Gly Ala Ser Lys Arg Leu Gln Thr Ile Cys Met Ser Gly Thr
1               5                   10                  15

Gly Ile Arg Ser Val Thr Gly Thr Pro Tyr Trp Met Ser Pro Glu
            20                  25                  30

<210> SEQ ID NO 14
<211> LENGTH: 60
<212> TYPE: PRT
<213> ORGANISM: Saccharomyces cerevisiae

<400> SEQUENCE: 14

Asp Phe Gly Ala Ala Lys Lys Ile Ala Asn Asn Gly Thr Arg Leu Ala
1               5                   10                  15

Ser Met Asn Lys Ile Glu Asn Ala Asp Gly Glu His Glu Asp Val Thr
            20                  25                  30

His Val Ser Asp Ser Lys Ala Val Lys Asn Asn Glu Asn Ala Leu Leu
        35                  40                  45

Asp Met Met Gly Thr Pro Met Tyr Met Ala Pro Glu
    50                  55                  60

<210> SEQ ID NO 15
<211> LENGTH: 26
<212> TYPE: PRT
```

<213> ORGANISM: Homo sapiens

<400> SEQUENCE: 15

Asp Phe Gly Leu Ala Arg Glu Trp His Lys Thr Thr Gln Met Ser Ala
1               5                   10                  15

Ala Gly Thr Tyr Ala Trp Met Ala Pro Glu
            20                  25

<210> SEQ ID NO 16
<211> LENGTH: 28
<212> TYPE: PRT
<213> ORGANISM: Homo sapiens

<400> SEQUENCE: 16

Asp Phe Gly Thr Ser Lys Arg Leu Ala Gly Ile Asn Pro Cys Thr Glu
1               5                   10                  15

Thr Phe Thr Gly Thr Leu Gln Tyr Met Ala Pro Glu
            20                  25

<210> SEQ ID NO 17
<211> LENGTH: 30
<212> TYPE: PRT
<213> ORGANISM: Homo sapiens

<400> SEQUENCE: 17

Asp Phe Gly Leu Ala Thr Val Lys Ser Arg Trp Ser Gly Ser Gln Gln
1               5                   10                  15

Val Glu Gln Pro Thr Gly Ser Val Leu Trp Met Ala Pro Glu
            20                  25                  30

<210> SEQ ID NO 18
<211> LENGTH: 27
<212> TYPE: PRT
<213> ORGANISM: Homo sapiens

<400> SEQUENCE: 18

Asp Phe Gly Cys Ser Val Lys Leu Thr Met Pro Gly Glu Val Asn Ser
1               5                   10                  15

Thr Leu Gly Thr Ala Ala Tyr Met Ala Pro Glu
            20                  25

<210> SEQ ID NO 19
<211> LENGTH: 11
<212> TYPE: PRT
<213> ORGANISM: Artificial Sequence
<220> FEATURE:
<223> OTHER INFORMATION: Artificially Synthesized Peptide Sequence

<400> SEQUENCE: 19

Met Ala Ser Met Thr Gly Gly Gln Gln Met Gly
1               5                   10